(12) United States Patent
Tezuka et al.

(10) Patent No.: US 11,857,157 B2
(45) Date of Patent: Jan. 2, 2024

(54) FLEXIBLE TUBE INSERTION SUPPORT APPARATUS, FLEXIBLE TUBE INSERTION APPARATUS, AND FLEXIBLE TUBE INSERTION METHOD

(71) Applicant: c/o OLYMPUS CORPORATION, Toyko (JP)

(72) Inventors: Ryo Tezuka, Hachioji (JP); Hirokazu Nishimura, Hachioji (JP); Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1014 days.

(21) Appl. No.: 16/697,471

(22) Filed: Nov. 27, 2019

(65) Prior Publication Data

US 2020/0093353 A1 Mar. 26, 2020

Related U.S. Application Data

(63) Continuation of application No. PCT/JP2017/020482, filed on Jun. 1, 2017.

(51) Int. Cl.
*A61B 1/00* (2006.01)
*A61B 1/005* (2006.01)
(Continued)

(52) U.S. Cl.
CPC ...... *A61B 1/00055* (2013.01); *A61B 1/00009* (2013.01); *A61B 1/009* (2022.02);
(Continued)

(58) Field of Classification Search
CPC . A61B 1/00055; A61B 1/009; A61B 1/00096; A61B 1/00097; A61B 1/00009;
(Continued)

(56) References Cited

U.S. PATENT DOCUMENTS

2005/0228221 A1 10/2005 Hirakawa
2010/0191056 A1 7/2010 Tanaka
(Continued)

FOREIGN PATENT DOCUMENTS

JP 2000-342520 A 12/2000
JP 2004-358095 A 12/2004
(Continued)

OTHER PUBLICATIONS

International Search Report dated Aug. 15, 2017 received in PCT/JP2017/020482.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A flexible tube insertion support apparatus includes a generation section configured to generate propriety information regarding a propriety of a twisting operation of a flexible tube in accordance with a force quantity of an external force applied to the flexible tube when the flexible tube is twisted in a counterclockwise direction or a clockwise direction around a central axis of the flexible tube. The external force is detected by at least one external force detector that is disposed on the flexible tube to be inserted into the subject and configured to detect the external force. The flexible tube insertion support apparatus also includes an output section configured to output the propriety information generated by the generation section.

19 Claims, 18 Drawing Sheets

(51) Int. Cl.
  *A61B 1/04* (2006.01)
  *A61B 5/06* (2006.01)
(52) U.S. Cl.
  CPC ........ *A61B 1/0057* (2013.01); *A61B 1/00096* (2013.01); *A61B 1/00097* (2022.02); *A61B 5/061* (2013.01); *A61B 5/065* (2013.01); *A61B 1/044* (2022.02)
(58) Field of Classification Search
  CPC ....... A61B 1/0057; A61B 1/044; A61B 5/061; A61B 5/065
  See application file for complete search history.

(56) References Cited

U.S. PATENT DOCUMENTS

| | | | |
|---|---|---|---|
| 2015/0099925 | A1 | 4/2015 | Davidson et al. |
| 2015/0209056 | A1* | 7/2015 | Shoham ................. A61B 34/30 606/80 |
| 2017/0049298 | A1* | 2/2017 | Hunter ................... A61B 5/067 |
| 2017/0181808 | A1* | 6/2017 | Panescu ................. A61B 34/20 |
| 2018/0042680 | A1* | 2/2018 | DiMaio ................... G16H 20/40 |
| 2018/0177556 | A1* | 6/2018 | Noonan .................. A61B 34/10 |
| 2018/0338806 | A1* | 11/2018 | Grubbs ................. A61B 34/30 |
| 2019/0239723 | A1* | 8/2019 | Duindam ............... A61B 34/76 |

FOREIGN PATENT DOCUMENTS

| | | |
|---|---|---|
| JP | 2006-89825 A | 4/2006 |
| JP | 2009-90023 A | 4/2009 |
| JP | 4274854 B2 | 6/2009 |
| JP | 2013-223735 A | 10/2013 |
| JP | 2015-196075 A | 11/2015 |
| WO | 2016-098255 A1 | 6/2016 |

OTHER PUBLICATIONS

English translation of International Preliminary Report on Patentability dated Dec. 12, 2019, together with the Written Opinion received in related International Application No. PCT/JP2017/020482.

* cited by examiner

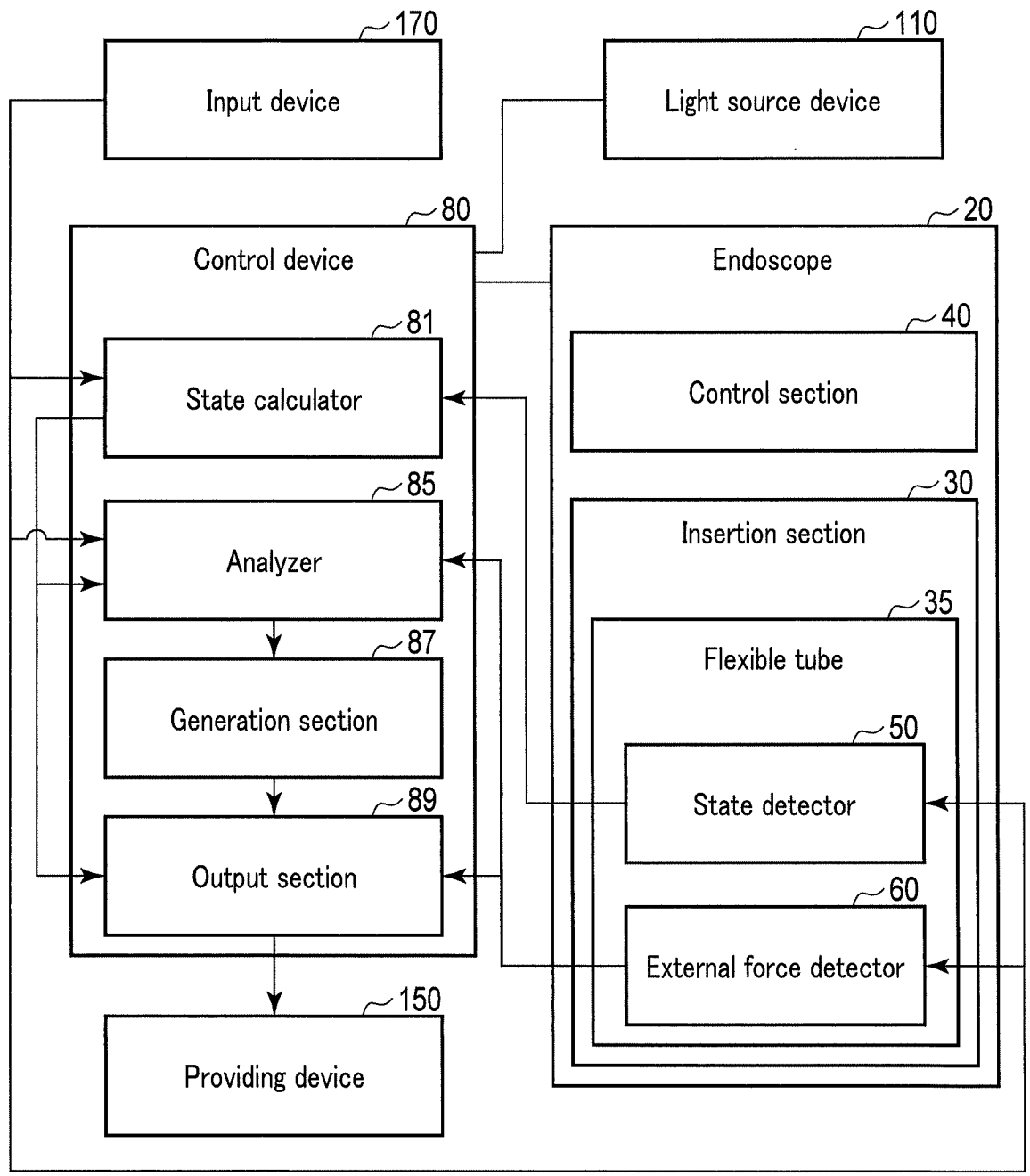
F I G. 2

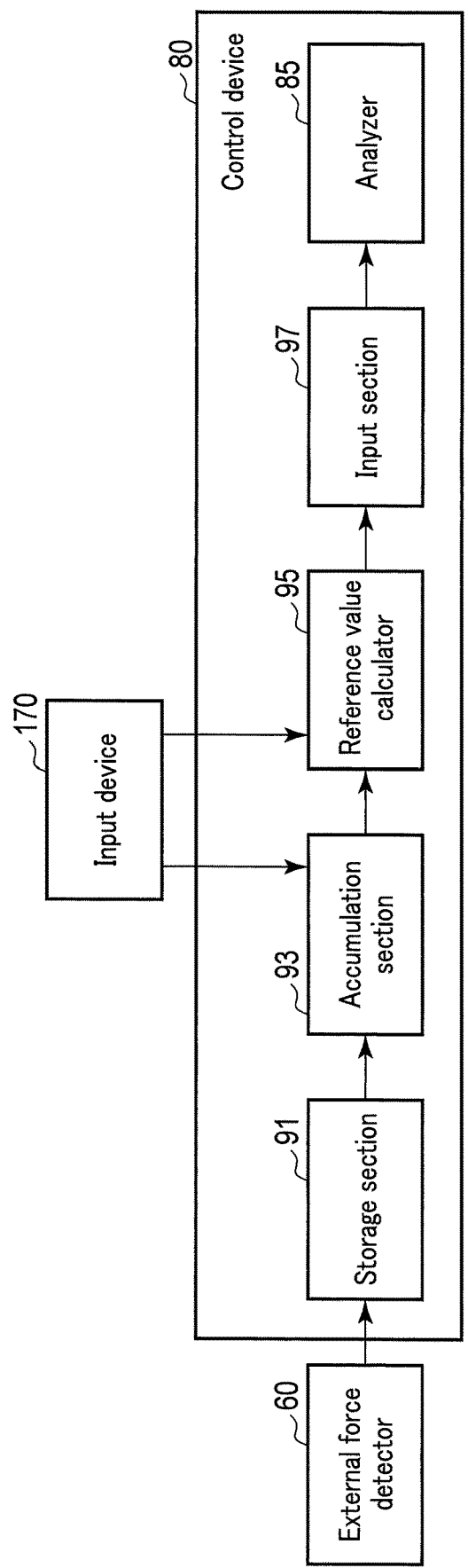
F I G. 5B

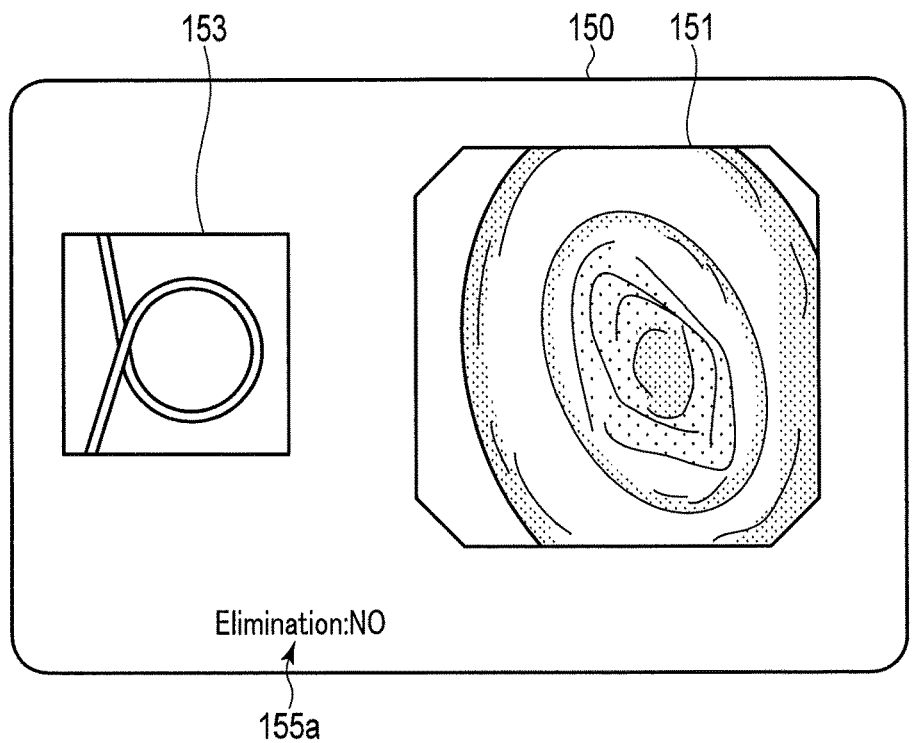
F I G. 7A
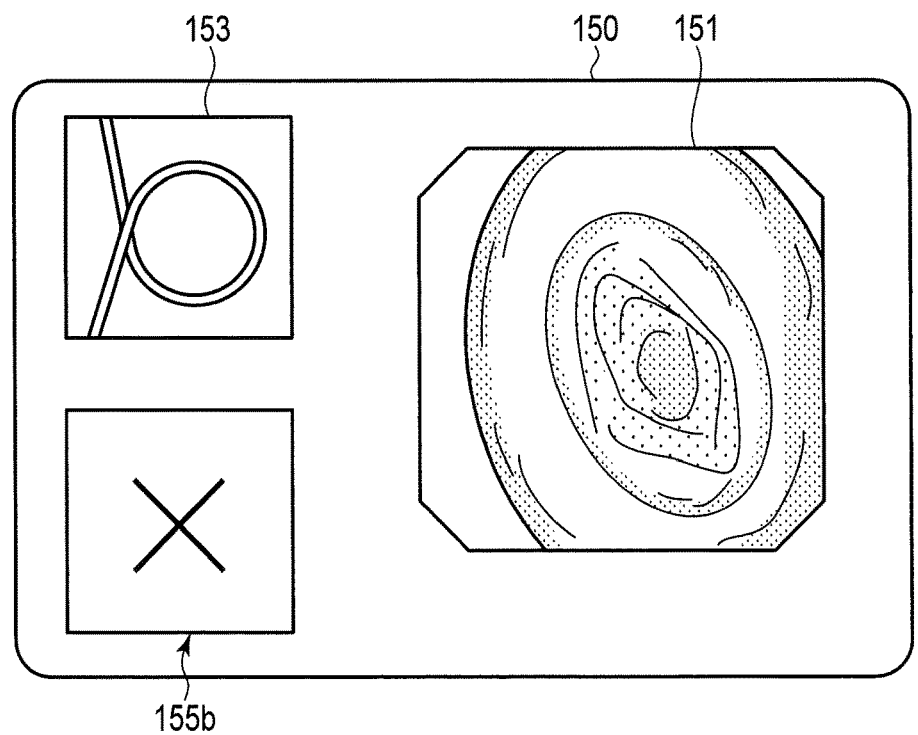
F I G. 7B

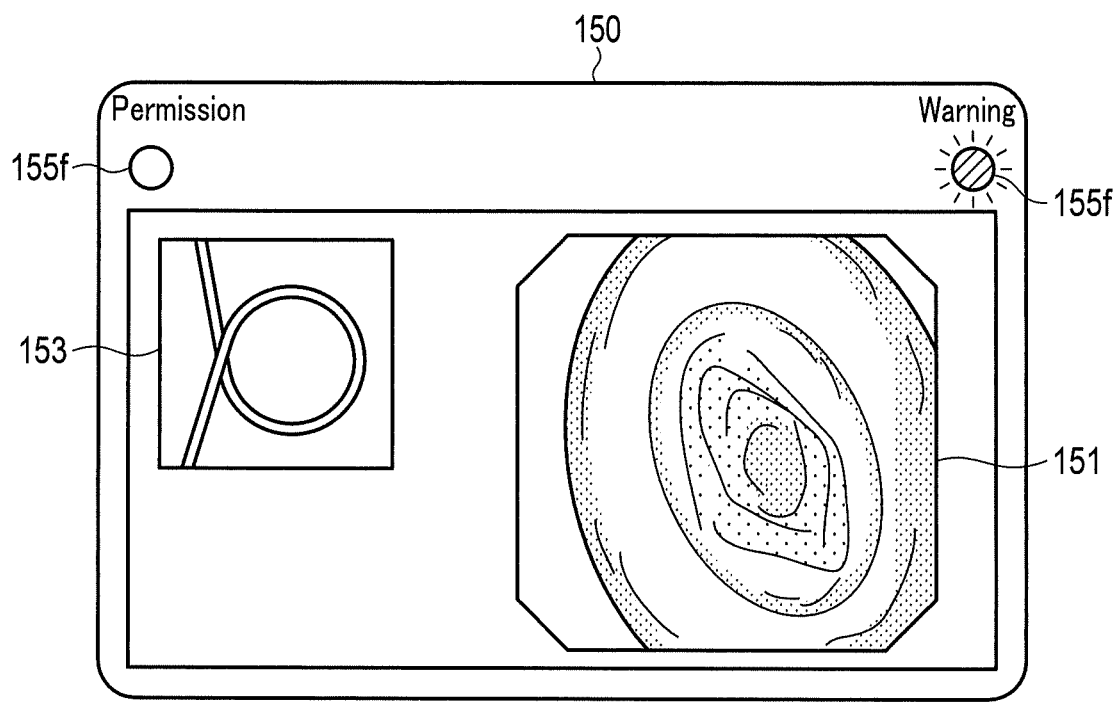
F I G. 7C
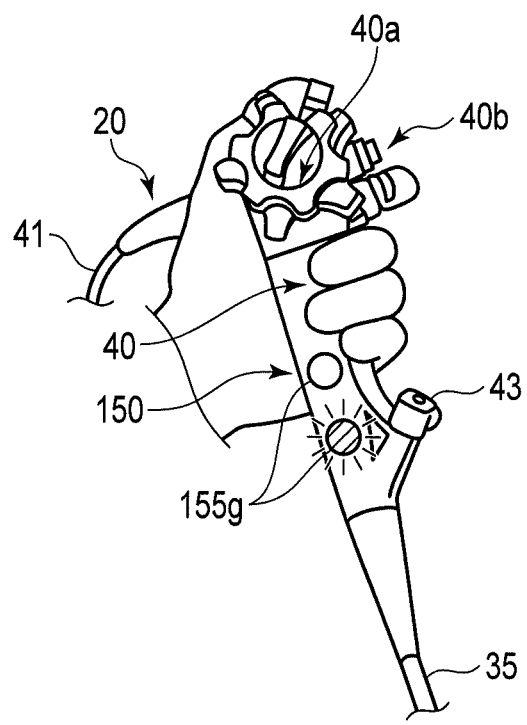
F I G. 7D

FLEXIBLE TUBE INSERTION SUPPORT APPARATUS, FLEXIBLE TUBE INSERTION APPARATUS, AND FLEXIBLE TUBE INSERTION METHOD

CROSS-REFERENCE TO RELATED APPLICATIONS

This application is a Continuation Application of PCT Application No. PCT/JP2017/020482, filed Jun. 1, 2017, the entire contents of which are incorporated herein by reference.

BACKGROUND OF THE INVENTION

1. Field of the Invention

The present invention relates to a flexible tube insertion support apparatus configured to insert a flexible tube toward a deep part of a pipeline section of a subject into which a flexible tube is inserted, a flexible tube insertion apparatus, and a flexible tube insertion method.

2. Description of the Related Art

When a flexible tube of an endoscope is inserted into a large intestine, especially a sigmoid colon, a loop section may be formed in the flexible tube. The formation of such a loop section within the sigmoid colon may increase the difficulty of insertion (progression) into the deep part such as a descending colon, and also may cause the large intestine to stretch, which may cause a patient pain. Therefore, it is necessary that the formed loop section is eliminated and the flexible tube is changed into a substantially linear state. In general, the loop section is eliminated and the flexible tube is changed into the substantially linear state by a twisting (rotation) operation in the insertion technique for the flexible tube.

However, when the flexible tube is changed in shape by such a twisting operation, the changing flexible tube may cause the large intestine to stretch, which may cause a patient pain. Thus, an operator needs to make an appropriate determination for each patient before performing a twisting operation, as to whether or not the twisting operation should be performed to eliminate the loop section and change the flexible tube into the substantially liner state.

Furthermore, during a twisting operation, the application of excessive quantity of twisting force to the flexible tube results in a rapid change in shape of the flexible tube and rapid elimination of the loop section. This elimination overloads a patient and causes him or her pain. Thus, it is necessary that an operator makes an appropriate determination for each patient as to whether an excessive quantity of force is applied or not during a twisting operation in progress.

Generally, a running state of the flexible tube inside the large intestine, a length of the large intestine, and a condition of the large intestine differ widely for each patient depending on his or her sex, age, preexisting disorder, surgical history, current condition, etc. Such differences give variety to the tactile information for an operator when performing a twisting operation of the flexible tube using one hand while gripping the hand side of the flexible tube with the same hand, such tactile information being a sense of resistance of the flexible tube, which is transmitted from the hand side of the flexible tube to the same hand and is sensed differently by different operators. It is not easy for an operator to sense such resistance or a difference in resistance, and based on such sense of resistance, determine in advance of a twisting operation whether or not to perform the twisting operation and determine during the operation whether or not an excessive quantity of force is applied. This is even more difficult for an operator with less experience in the twisting operation (hereinafter, referred to as an inexperienced person).

As described above, the insertion technique used for a large intestine endoscope examination is highly difficult and requires skill. Therefore, there is a demand for support information for insertion to be provided when the insertion technique is performed.

Under this circumstance, for example, Japanese Patent No. 4,274,854 discloses an endoscope insertion shape analyzing apparatus that calculates a position of a flexible tube inserted into a body cavity using a magnetic coil, etc., and analyzes a loop section based on the calculated position. As support information, the endoscope insertion shape analyzing apparatus provides a linearization operation method by which the loop section is eliminated based on an analysis result and the flexible tube is changed into a substantially linear state. As the linearization operation method, the endoscope insertion shape analyzing apparatus provides (displays) on its display, a twisting direction of the flexible tube for the elimination of the loop section.

BRIEF SUMMARY OF THE INVENTION

An aspect of the present invention is directed to a flexible tube insertion support apparatus. The flexible tube insertion support apparatus includes a generation section configured to generate propriety information regarding a propriety of a twisting operation of a flexible tube in accordance with a force quantity of an external force applied to the flexible tube when the flexible tube is twisted in a counterclockwise direction or a clockwise direction around a central axis of the flexible tube. The external force is detected by at least one external force detector that is disposed on the flexible tube to be inserted into the subject and configured to detect the external force. The flexible tube insertion support apparatus also includes an output section configured to output the propriety information generated by the generation section.

An aspect of the present invention is directed to a flexible tube insertion apparatus. The flexible tube insertion apparatus includes a flexible tube that has flexibility and is to be inserted into a subject, at least one external force detector that is disposed on the flexible tube and configured to detect an external force applied to the flexible tube and calculate a force quantity of the detected external force, the above mentioned flexible tube insertion support apparatus, and a providing device configured to provide the propriety information output from the output section.

An aspect of the present invention is directed to a flexible tube insertion support method of supporting insertion of a flexible tube to be inserted into a subject. The flexible tube insertion support method includes, when the flexible tube is twisted in a counterclockwise direction or a clockwise direction around a central axis of the flexible tube, detecting an external force applied to the flexible tube, generating propriety information regarding a propriety of a twisting operation of the flexible tube in accordance with a force quantity of the external force, and outputting the generated propriety information.

Advantages of the invention will be set forth in the description that follows, and in part will be obvious from the description, or may be learned by practice of the invention.

The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram for explaining a relation among a state detector, a state calculator, an external force detector, an analyzer, a generation section, an output section, a providing device, and an input device.

FIG. 5B is a diagram showing an example of a constitution of inputting the reference value to the analyzer.

FIG. 7A shows an example of providing propriety information.

FIG. 7B shows an example of providing propriety information.

FIG. 7C shows an example of providing propriety information.

FIG. 7D shows an example of providing propriety information.

DETAILED DESCRIPTION OF THE INVENTION

Hereinafter, an embodiment of the present invention will be described with reference to the drawings. In some of the drawings, the members are partly omitted for clarification of illustration.

Figure 1:
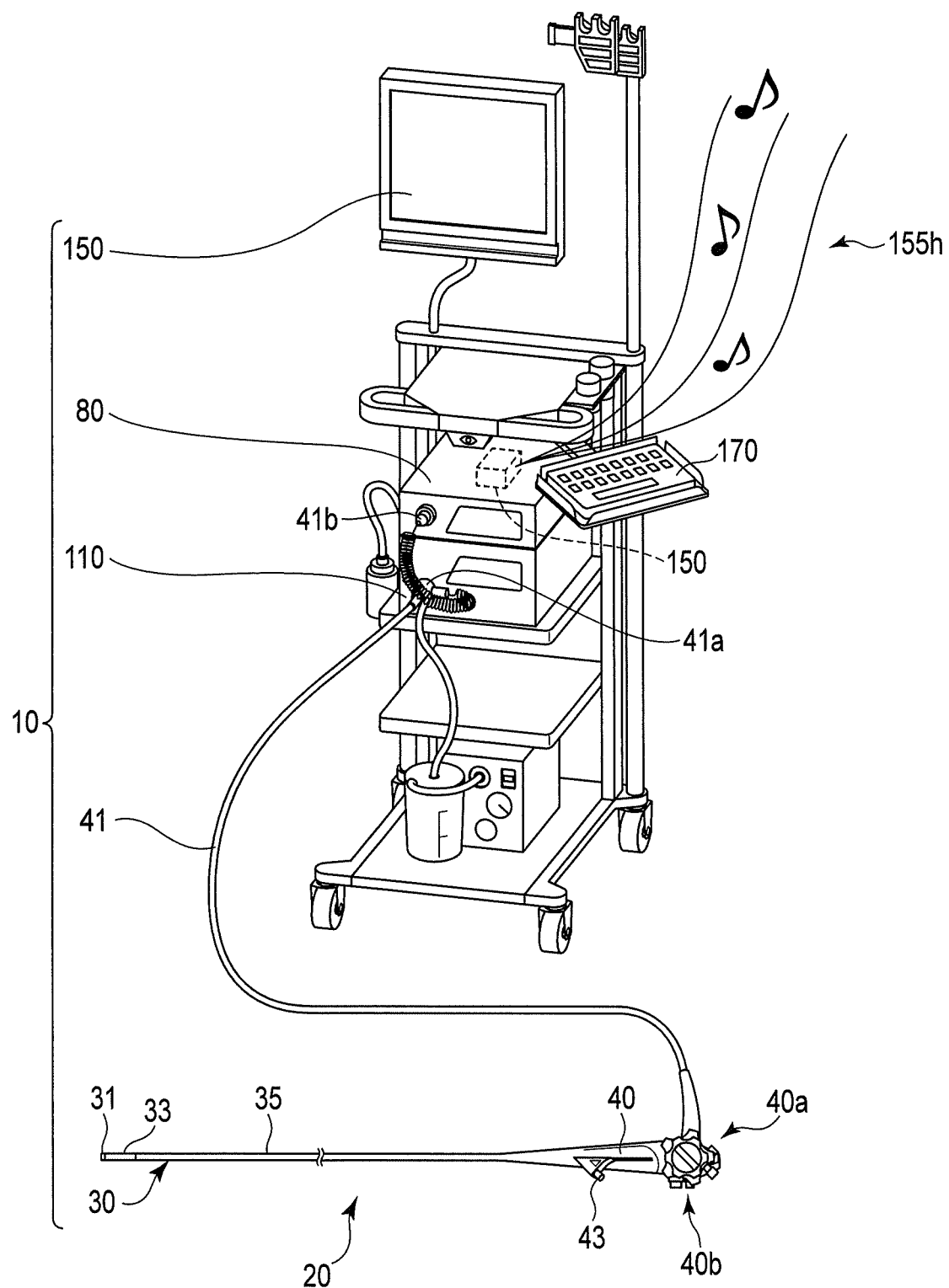
FIG. 1 is a schematic view of a flexible tube insertion apparatus according to an embodiment of the present invention.

As shown in FIG. 1, a flexible tube insertion apparatus (hereinafter, referred to as insertion apparatus 10) includes an endoscope 20, a control device 80 that functions as a flexible tube insertion support apparatus, a light source device 110, a providing device 150, and an input device 170. The control device 80 is connected to the endoscope 20, the light source device 110, the input device 170, and the providing device 150, and controls driving of them. The control device 80 functions as the flexible tube insertion support apparatus configured to output support information for supporting an insertion operation of a flexible tube 35 of an insertion section 30 disposed on the endoscope 20, for example.

The light source device 110 emits illumination light for the endoscope 20 to perform observation and imaging.

The control device 80 may function as a video processor having an image processing circuit (not shown) electrically connected to an imaging unit (not shown). The imaging unit is embedded in a distal end section of the insertion section 30, and has, for example, a CCD, etc. The imaging unit converts, into an electrical signal, an optical image obtained from reflected light generated by reflecting the illumination light emitted from the distal end section of the insertion section 30 on an observation object (for example, an inner wall of a pipeline section of a subject into which the insertion section is inserted). The imaging unit outputs the electrical signal to the image processing circuit. The image processing circuit generates an image signal of the observation object based on the electrical signal.

The providing device 150 provides first propriety information and second propriety information to be described later. An example of such provision will be described later. The providing device 150 may provide an image 151 (e.g., see FIG. 7A) of the observation object based on the image signal generated by the image processing circuit. In this case, the providing device 150 has, for example, a monitor to display the image 151.

The input device 170 is, for example, a general input device such as a keyboard. The input device 170 may be, for example, a pointing device such as a mouse, a tag reader, a button switch, a slider, a dial, or a foot switch. The input device 170 may be used by an operator to input various commands for causing the insertion apparatus 10 to operate. The input device 170 as the button switch may be embedded in a control section 40 of the endoscope 20.

The endoscope 20 is, for example, a medical soft endoscope. The endoscope 20 may be, for example, an industrial soft endoscope, a catheter, or a treatment instrument. The endoscope 20 is only required to have the soft insertion section 30 to be inserted into a pipeline section (for example, an intestinal tract of a large intestine) of a subject (for example, a patient). The insertion section 30 is only required to have a flexible portion (for example, the flexible tube 35)

that is flexible in receipt of an external force. The endoscope 20 may be a front-viewing endoscope, or a side-viewing endoscope. The endoscope 20 is an example of a small precision apparatus. In addition to the endoscope 20, examples of the small precision apparatus include a probe 190 (see FIG. 4B) to be described later. A subject is not limited to, for example, a human, and may be an animal or any other structural object. The pipeline section may be, for example, a pipe for an industrial use.

The endoscope 20 has the insertion section 30, the control section 40 that is connected to the proximal end section of the insertion section 30 and configured to control the endoscope 20, and a universal cord 41 extending from a side surface of the control section 40. The universal cord 41 has a connection section 41a that is detachably attached to the light source device 110 and a connection section 41b that is detachably detached to the control device 80. The light source device 110 may be electrically connected to the control device 80, and the endoscope 20 may be electrically connected to the control device 80 through the light source device 110 by providing the connection section 41a with an electrical contact.

The insertion section 30 is tubular, elongated, and flexible. The insertion section 30 advances and retreats within the pipeline section with respect to the pipeline section. The insertion section 30 is an insertion body to be inserted into the pipeline section. The insertion section 30 has a distal end hard section 31 and the flexible tube 35 in this order from the distal end section of the insertion section 30 to the proximal end section of the insertion section 30. The distal end hard section 31 is shorter than the flexible tube 35. Therefore, in the present embodiment, the distal end hard section 31 and a distal end section of the flexible tube 35 are deemed to be a distal end section of the insertion section 30. The distal end section of the flexible tube 35 has a bendable section 33. That is, it is deemed that the bendable section 33 serves as the distal end section of the flexible tube 35, and the bendable section 33 is included in the flexible tube 35. That is, the flexible tube 35 has the bendable section 33 that is actively bent under control of the control section 40, and a flexible section excluding the bendable section 33. The flexible section has flexibility, and is passively bent by an external force. The flexible section that is flexed by an external force is bendable according to the shape of the pipeline section. On the other hand, the bendable section 33 bends in a desired direction by a knob 40a disposed on the control section 40.

As shown in FIG. 2, the insertion apparatus 10 has the state detector 50 configured to detect state information of the flexible tube 35 regarding a state of the flexible tube 35 including the bendable section 33. The state information includes a bending state of the flexible tube 35 including the bendable section 33. The bending state of the flexible tube 35 includes, for example, the bending quantity (the magnitude of bending) of the flexible tube 35 including the bendable section 33. The bending quantity is, in other words, a curvature radius or curvature. The bending state of the flexible tube 35 includes a bending direction of the flexible tube 35 including the bendable section 33.

The state detector 50 has a fiber sensor configured to utilize loss in the light transmission quantity due to bending of an optical fiber 51 (see FIG. 4C), as an example. The fiber sensor has a light source (not shown) configured to emit light, the single optical fiber 51 configured to guide light, and a reflector (not shown) configured to reflect light so that the light guided by the optical fiber 51 proceeds reversely along the optical fiber 51. The fiber sensor has a light receiver (not shown) configured to receive the light reflected by the reflector and a light branching section (not shown). The state detector 50 includes constituent members that may be disposed separately in the endoscope 20 and the control device 80; however, for the sake of clarity of illustration, in FIG. 2, the state detector 50 is depicted in the flexible tube 35 as one portion in which the optical fiber 51 is disposed. The light source has, for example, an LED, etc. The light source is a separate entity from a light source of the light source device 110 configured to emit light for observation and imaging. The optical fiber 51 is embedded in the endoscope 20 and has flexibility. The optical fiber 51 has detection targets (not shown) mounted on the insertion section 30. The detection targets are disposed in different positions in the longitudinal axis direction of the optical fiber 51. For example, the detection targets may be disposed on portions for calculating shape information of the flexible tube 35, portions for detecting an external force applied to the flexible tube 35, and the like, which will be described later. In the present embodiment, the detection targets are disposed to be spaced apart from each other at equidistant intervals. The reflector is disposed on a distal end of the optical fiber 51 located at the distal end section of the insertion section 30. The reflector has, for example, a mirror. The light receiver may have, for example, a spectroscopic element such as a spectroscope or a color filter, and a light receiving element such as a photodiode. The light source, the light receiver, and the proximal end section of the optical fiber 51 are optically connected to the light branching unit. The light branching unit has, for example, an optical coupler or a half mirror. The light branching unit guides light emitted from the light source to the optical fiber 51, and also guides returned light reflected by the reflector and guided by the optical fiber 51 to the light receiver. That is, the light travels in the order of the light source, the light branching unit, the optical fiber 51, the reflector, the optical fiber 51, the light branching unit, and the light receiver. The light source, the light receiver, and the light branching unit are mounted on the control device 80, for example.

The fiber sensor is only required to have the light source, the optical fiber 51, and the light receiver (not shown) configured to receive light guided by the optical fiber 51. In this case, for example, the light receiver is disposed on the distal end section of the insertion section 30.

When the insertion section 30 is bent, the optical fiber 51 is bent in accordance with the bending. Accordingly, part of the light propagating through the optical fiber 51 exits (leaks) to the outside through, for example, the detection targets each having sensitivity to a different wavelength. The detection target changes optical characteristics of the optical fiber 51, for example, light transmission quantity of light of a predetermined wavelength. Therefore, when the optical fiber 51 is bent, the light transmission quantity of the light guided into the optical fiber 51 is changed according to the bending quantity of the optical fiber 51. An optical signal including information on this change in the light transmission quantity is received by the light receiver. The light receiver outputs the optical signal as state information to a state calculator 81 disposed on the control device 80, which will be described later.

A single detection target may be disposed in a single optical fiber 51, and in this case, optical fibers 51 are disposed. Assume that the detection targets are disposed at the same position or close positions in the longitudinal axis direction of the optical fiber 51 and at different positions in a direction around the central axis in the longitudinal axis direction of the optical fiber 51. In this case, a combination of the detection results of the detection target enables the detection of the bending quantity and the bending direction.

The state detector 50 is not limited to having the fiber sensor. The state detector 50 may have, for example, any one of a strain sensor, an acceleration sensor, a gyro sensor, an element such as a coil, and a position sensor. The strain sensor detects, for example, a bending strain generated in the flexible tube 35 by an external force (pressure) that the flexible tube 35 receives from the outside of the flexible tube 35 (e.g., an inner peripheral wall section of the pipeline section). The acceleration sensor detects an acceleration of the flexible tube 35. The gyro sensor detects an angular velocity of the flexible tube 35. The element is of a magnetic type that generates a magnetic field in accordance with a state of the flexible tube 35, such as a shape of the flexible tube 35. The position sensor detects a position of the flexible tube 35.

The state detector 50 constantly performs the detection (operation) after a detection start instruction is input from the input device 170 to the state detector 50. The detection may be performed every time a certain time elapses, and timing for the detection is not particularly limited. The state detector 50 is connected to the state calculator 81 by, for example, wire or wireless means, and outputs a detection result detected by the state detector 50 to the state calculator 81.

As shown in FIG. 2, the insertion apparatus 10 has one or more external force detectors 60, the state calculator 81, an analyzer 85, a generation section 87, and an output section 89. The external force detector 60 is disposed on, for example, the flexible tube 35. The state calculator 81, the analyzer 85, the generation section 87, and the output section 89 are disposed on the control device 80, for example. The control device 80, which functions as the flexible tube insertion support apparatus, outputs first propriety information and second propriety information, which will be described later, as support information for insertion.

The state calculator 81, the analyzer 85, the generation section 87, and the output section 89 are constituted by, for example, a hardware circuit including an ASIC, etc. At least one of the state calculator 81, the analyzer 85, the generation section 87, and the output section 89 may be constituted by a processor. In the case where at least one of the state calculator 81, the analyzer 85, the generation section 87, and the output section 89 is constituted by a processor, an internal or an external memory (not shown) accessible by a computer is disposed. The internal memory or the external memory stores a program code to be executed by a processor so that the processor is caused to function as at least one of the state calculator 81, the analyzer 85, the generation section 87, and the output section 89. The state calculator 81, the analyzer 85, the generation section 87, and the output section 89 may be constituted by using a processor or using processors. In the latter case, it is possible to transmit and receive data between the processors so that data is processed by the processors in cooperation with each other. Furthermore, in the latter case, it is possible to dispose the processors within separate housings.

The analyzer 85, the generation section 87, and the output section 89 may be disposed on the control section 40 as long as they are constituted by a hardware circuit.

The state calculator 81 calculates shape information of the flexible tube 35 including the bendable section 33, regarding the shape of the flexible tube 35 including the bendable section 33 along the central axis of the flexible tube 35, based on the state information detected by the state detector 50. In particular, the state calculator 81 calculates shape information, to be more specific, a bent shape of a portion that is actually bent in the flexible tube 35, based on the state information output from the state detector 50, for example. The bent shape includes the bending quantity and the bending direction of the flexible tube 35 including the bendable section 33, for example. The shape information includes position information of the external force detector 60. For example, since the position information of the external force detector 60 in the flexible tube 35 is preset, the shape information includes the position information of the external force detector 60 by overlapping a position of the external force detector 60 with the calculated bent shape. In addition, the state calculator 81 may calculate the position information of the external force detector 60 based on an output of a sensor 61a, which will be described later, of the external force detector 60.

The state calculator 81 may output the shape information calculated by the state calculator 81 to the providing device 150 through the output section 89, and the providing device 150 may display the shape information as an image 153 (for example, see FIG. 7A). The image 153 may indicate the position of the external force detector 60 in the shape information. The state calculator 81 may output the shape information to the analyzer 85 so that the analyzer 85 analyzes based on the shape information whether or not the flexible tube is in a substantially linear state. The state calculator 81 constantly performs the calculation (operation) after a calculation start instruction output from the input device 170 is input to the state calculator 81 in a state in which a detection result by the state detector 50 is input. The calculation may be performed every time a certain time elapses, and timing for the calculation is not particularly limited.

The external force detector 60 is disposed on the flexible tube 35, detects an external force applied to the flexible tube 35, and calculates a value of the detected external force. As shown in FIGS. 3A, 3B, 3C, 3D, and 3E, for example, assume that the hand side of the flexible tube 35 is twisted in each of a counterclockwise direction and a clockwise direction around the central axis of the flexible tube 35 by an operator's one hand while the hand side is gripped by this one hand. Here, each of the counterclockwise direction and the clockwise direction indicates a direction around the central axis of the flexible tube 35 when the distal end section side of the flexible tube 35 is viewed from the hand side of the flexible tube 35 in the central axis direction of the flexible tube 35. In such a twisting operation, for example, a left twisting operation in the counterclockwise direction is performed, and after the left twisting operation, a right twisting operation in the clockwise direction is performed. The right twisting operation follows the left twisting operation. The order of the left twisting operation and the right twisting operation is not particularly limited. A time interval between the left twisting operation and the right twisting operation may be adjusted as desired. An operator's twisting force applied from his or her one hand to the hand side of the flexible tube 35 is transmitted from the hand side of the flexible tube 35 to the distal end section side of the flexible tube 35. As a result, the flexible tube 35 is twisted in each of the counterclockwise direction and the clockwise direction around the central axis of the flexible tube 35. At this time, the external force detector 60 detects, as an external force, each of a twisting force in the counterclockwise direction (hereinafter, referred to as external force LF) and a twisting force in the clockwise direction (hereinafter, referred to as external force RF). The external force detector 60 detects the external force LF in the counterclockwise direction and the external force RF in the clockwise direction, and calculates a force quantity of the external force LF (hereinafter, referred to as force quantity LAF) and a force quantity of the external force RF (hereinafter, referred to as force quantity RAF). Specifically, the external force detector 60 calculates the force quantity LAF based on the detected external force LF, and calculates the force quantity RAF based on the detected external force RF. In other words, the external force detector 60 measures the force quantities LAF and RAF of the external forces LF and RF both applied to the flexible tube 35 at a position of the external force detector 60. Therefore, the force quantities LAF and RAF correspond to measured values measured by the external force detector 60, values of the detected external forces LF and RF, and also quantitative information. In this way, the external force detector 60 calculates the force quantities LAF and RAF as measured values. The external force detector 60 may detect not only a twisting force but also other forces. An example of other forces includes a reaction force that the flexible tube 35 receives from the intestinal wall around the flexible tube 35 or the organs around the flexible tube 35.

The external force detector 60 outputs the force quantities LAF and RAF to the analyzer 85. The external force detector 60 constantly performs the detection (operation) after a detection start instruction output from the input device 170 is input to the external force detector 60. The detection may be performed every time a certain time elapses, and timing for the detection is not particularly limited.

Here, examples 1 to 3 of a constitution of the external force detector 60 will be described.

Figure 4A:
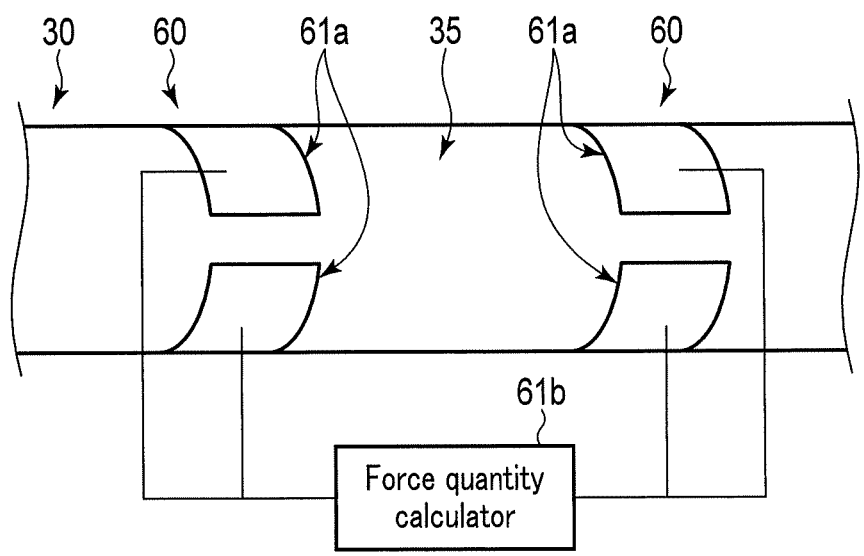
FIG. 4A is a diagram showing an example of a constitution of the external force detector.

As shown in FIG. 4A, as the example 1, the external force detector 60 may have one or more sensors 61a. As in the state detector 50, the sensor 61a may have, for example, any of a strain sensor, an acceleration sensor, a gyro sensor, an element such as a coil, a position sensor, and a fiber sensor. For example, the sensor 61a is disposed on a peripheral surface of the flexible tube 35. For example, the sensor 61a is disposed directly on an outer peripheral surface of the flexible tube 35. For example, the sensors 61a may be disposed to be spaced apart from each other at equidistant intervals in the direction around the central axis of the flexible tube 35. In addition, in the case of external force detectors 60 being disposed on the flexible tube 35, for example, the external force detectors 60 are disposed to be spaced apart from each other at equidistant intervals in the direction of the central axis of the flexible tube 35, and the sensors 61a on each external force detector 60 may be disposed to be spaced apart from each other at equidistant intervals in the direction of the central axis of the flexible tube 35. Each of the sensors 61a detects, as the external forces LF and RF, bending strains that are generated in the flexible tube 35 due to the twisting when the flexible tube 35 is twisted in each of the counterclockwise direction and the clockwise direction around the central axis of the flexible tube 35. The sensors 61a output the external forces LF and RF to a force quantity calculator 61b. The force quantity calculator 61b calculates the force quantity LAF based on the external force LF and calculates the force quantity RAF based on the external force RF. The force quantity calculator 61b outputs the calculated force quantities LAF and RAF to the analyzer 85. As in the state calculator 81, the force quantity calculator 61b may be constituted by, for example, a hardware circuit including an ASIC, etc., or may be constituted by a processor.

The force quantity calculator 61b may be disposed on the control device 80, or may be disposed on the control section 40. Although not shown in this example, the external force detector 60 may also serve as both the state detector 50 having the sensors 61a and the state calculator 81. In such a case, the external force detector 60 detects, as the state detector 50, the state information from the outputs of the sensors 61a and detects the external forces LF and RF. The external force detector 60 calculates as the state calculator 81 the shape information and also calculates the force quantities LAF and RAF.

Figure 4B:
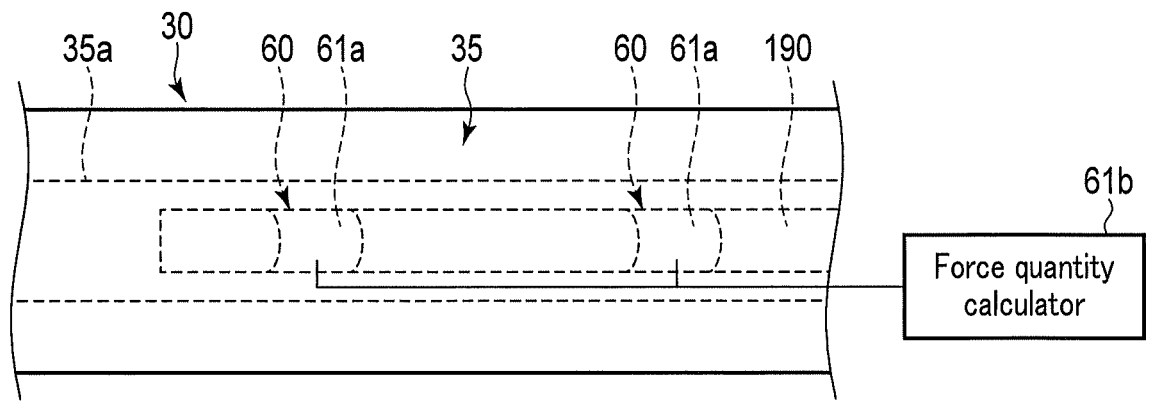
FIG. 4B is a diagram showing an example of a constitution of the external force detector.

As shown in FIG. 4B, as the example 2, it may be configured that the insertion apparatus 10 has the probe 190, and one or more sensors 61a are disposed on a peripheral surface of the probe 190. In this example, therefore, the external force detector 60 has one or more sensors 61a disposed on the peripheral surface of the probe 190. For example, the sensor 61a is disposed directly on an outer peripheral surface of the probe 190. In the case of external force detectors 60 being disposed on the probe 190, for example, the external force detectors 60 are disposed to be spaced apart from each other at equidistant intervals in the direction of the central axis of the probe 190, and the strain sensors on each external force detector 60 may be disposed to be spaced apart from each other at equidistant intervals in the direction of the central axis of the probe 190. Although not shown, the sensors 61a may be disposed to be spaced apart from each other at equidistant intervals, for example, in the direction around the central axis of the probe 190.

The probe 190 is a separate entity from the flexible tube 35. The probe 190 has flexibility and is inserted into a channel 35a disposed inside the flexible tube 35 from an insertion port section 43 (see FIG. 1) disposed on the control section 40. The outer peripheral surface of the probe 190 can abut on an inner peripheral surface of the channel 35a. The abutting is performed, for example, when the flexible tube 35 is bent. The probe 190 can be inserted and extracted freely into and from the flexible tube 35. Such a probe 190 is deemed to be an insertion body that is inserted into the pipeline section through the flexible tube 35. The probe 190 is positioned relative to the flexible tube 35 in the direction of the central axis of the flexible tube 35 and the direction around the axis of the central axis thereof. Therefore, the sensors 61a disposed on the probe 190 are indirectly disposed on the flexible tube 35 through the probe 190. When the external force is applied to the flexible tube 35, the flexible tube 35 is flexed. The probe 190 is flexed in accordance with the flexing of the flexible tube 35. As a result, the outer peripheral surface of the probe 190 abuts on the inner peripheral surface of the channel 35a. When the external force LF or RF is applied to the flexed flexible tube 35, the flexible tube 35 is twisted in accordance with the external force LF or RF. For example, the external forces LF and RF are applied (transmitted) to the probe 190 through the abutting portion. The probe 190 is twisted in accordance with this twisting of the flexible tube 35, in other words, in accordance with the external force LF or RF applied to the probe 190. The sensors 61a detect the external forces LF and RF applied to the probe 190 through the flexible tube 35 and detect the external forces LF and RF as the external forces LF and RF applied to the flexible tube 35.

Figure 4C:
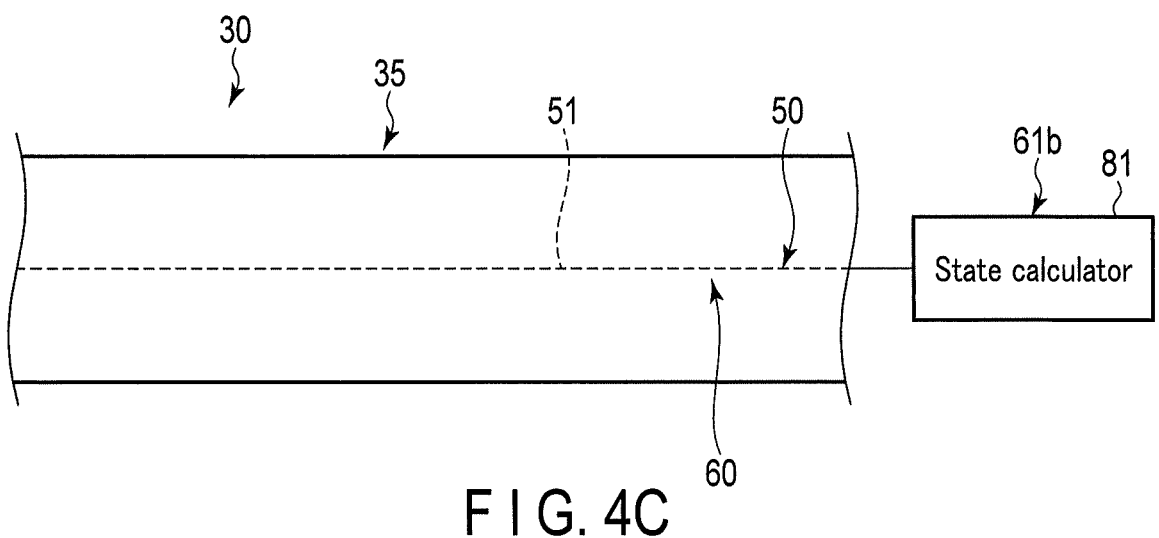
FIG. 4C is a diagram showing an example of a constitution of the external force detector.

As shown in FIG. 4C, as the example 3, the state detector 50 as the fiber sensor and the state calculator 81 may have a function of the external force detector 60. The state detector 50 detects the external forces LF and RF along with the state information. In addition, the state calculator 81 calculates the force quantities LAF and RAF along with the shape information. That is, the state calculator 81 functions as the force quantity calculator 61*b* configured to calculate the force quantities LAF and RAF.

The analyzer 85 analyzes a relation among the force quantity LAF of the external force LF in the counterclockwise direction, the force quantity RAF of the external force RF in the clockwise direction, and a reference value to be described later, in which the force quantity LAF and the force quantity RAF are detected by the external force detector 60 when the flexible tube 35 is twisted in each of the counterclockwise direction and the clockwise direction around the central axis of the flexible tube 35. In an example of the analysis, the analyzer 85 compares each of the force quantity LAF of the external force LF in the counterclockwise direction and the force quantity RAF of the external force RF in the clockwise direction with the reference value. The reference value is commonly used for these two force quantities LAF and RAF. Instead of the single reference value, reference values that are values respectively set for the two force quantities LAF and RAF may be used. Herein, the analyzer 85 makes a comparison between the force quantity LAF and the reference value, and a comparison between the force quantity RAF and the reference value. The order of making these comparisons is not particularly limited. A time interval between these two comparisons may be adjusted as desired. The analyzer 85 determines whether or not both of the two force quantities LAF and RAF are larger than the reference value. The analyzer 85 outputs a determination result (comparison result) to the generation section 87. The analyzer 85 constantly performs the analysis and the determination after an analysis start instruction output from the input device 170 is input to the analyzer 85 in a state in which a calculation result by the external force detector 60 is input. In addition, the analysis and the determination may be performed every time a certain time elapses, and the timing for the analysis and the determination is not particularly limited.

Here, examples 1 to 5 of an arrangement position of the external force detector 60 and a comparison operation of the analyzer 85 corresponding to the respective examples 1 to 5 will be described with reference to FIGS. 3A, 3B, 3C, 3D, and 3E. For the comparison operation, the flexible tube 35 is assumed to be twisted in each of the counterclockwise direction and the clockwise direction around the central axis of the flexible tube 35. In such a twisting operation, for example, a left twisting operation in the counterclockwise direction is performed, and after the left twisting operation, a right twisting operation in the clockwise direction is performed. The right twisting operation follows the left twisting operation. The order of the left twisting operation and the right twisting operation is not particularly limited.

Figure 3A:
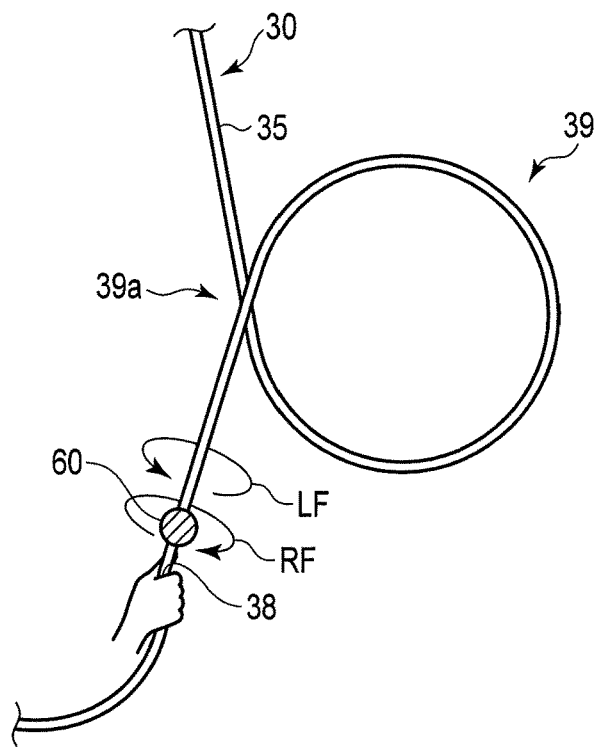
FIG. 3A is a diagram showing an example of an arrangement position of the external force detector.

As shown in FIG. 3A, as the example 1, for example, a single external force detector 60 is disposed on a gripped portion 38 of the flexible tube 35, which is to be gripped by an operator. The gripped portion 38 indicates an example of a position where an external force is applied to the flexible tube 35. The external force indicates, for example, an operator's gripping force. The gripped portion 38 indicates, for example, a position spaced by a desired length from the distal end section of the insertion section 30. The desired length indicates, for example, a total length of a rectum and a sigmoid colon, or a length greater than this total length. The external force detector 60 calculates the force quantities LAF and RAF at the gripped portion 38. The analyzer 85 compares each of the force quantity LAF and the force quantity RAF with the reference value.

Figure 3B:
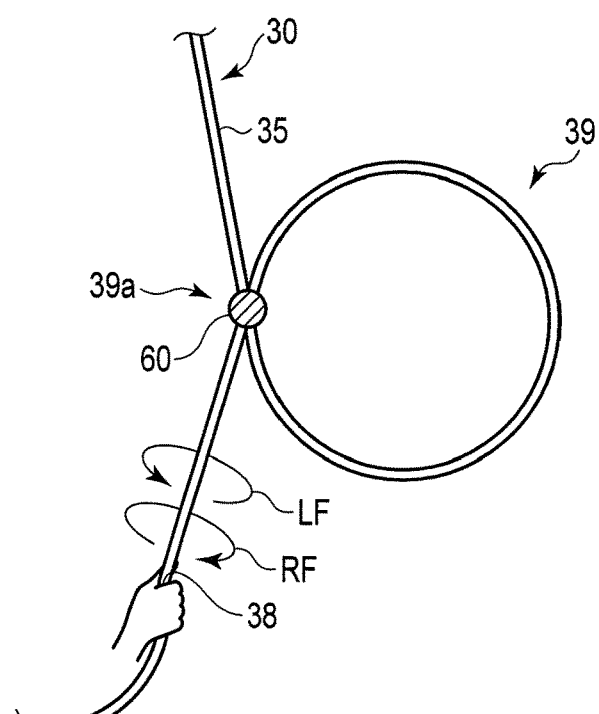
FIG. 3B is a diagram showing an example of an arrangement position of the external force detector.

As shown in FIG. 3B, as the example 2, for example, a single external force detector 60 is disposed on the periphery of an intersecting portion 39*a* including the intersecting portion 39*a* of a loop section 39 formed in the flexible tube 35. The periphery of the intersecting portion 39*a* indicates an example of a position where a reaction force due to twisting occurs. In general, the intersecting portion 39*a* is often formed in the sigmoid colon. Therefore, the periphery of the intersecting portion 39*a* indicates, for example, a position that is spaced by the length of the sigmoid colon from the distal end section of the insertion section 30. Although not clearly shown in FIG. 3B, in the periphery of the intersecting portion 39*a*, the external force detector 60 may be disposed on a side of the distal end section of the flexible tube 35, or may be disposed on a side of the proximal end section of the flexible tube 35. The external force detector 60 calculates force quantities LAF and RAF in the periphery of the intersecting portion 39*a*. The analyzer 85 compares each of the force quantity LAF and the force quantity RAF with the reference value.

Figure 3C:
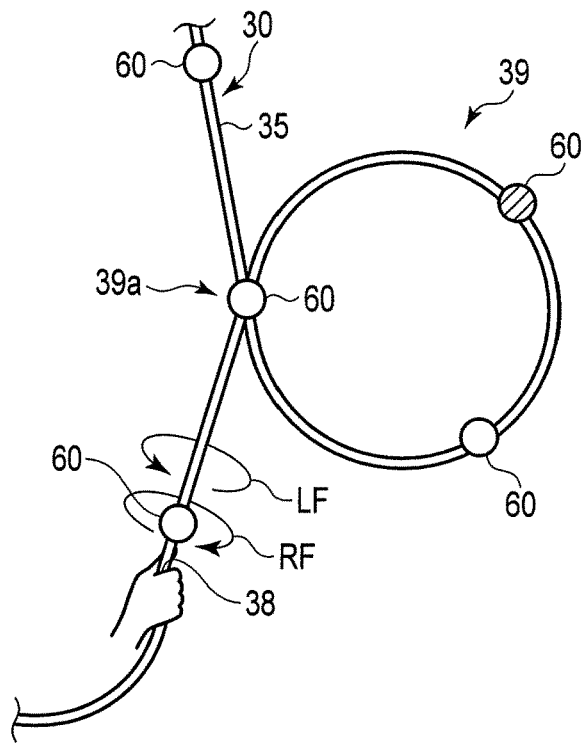
FIG. 3C is a diagram showing an example of an arrangement position of the external force detectors.

As shown in FIG. 3C, as the example 3, for example, external force detectors 60 are disposed to be spaced apart from each other at substantially equidistant intervals. For example, the external force detectors 60 are disposed within a range from the distal end section of the flexible tube 35 to the gripped portion 38. The external force detectors 60 calculate the force quantities LAF and RAF at their arrangement positions, respectively. For example, the analyzer 85 analyzes the maximum force quantity LAF among the force quantities LAF at the respective arrangement positions. The analyzer 85 compares each of the maximum force quantity LAF and the force quantity RAF at the arrangement position of the external force detector 60 that has calculated the maximum force quantity LAF, with the reference value. In FIG. 3C, the external force detector 60 that is used for the comparison by the analyzer 85 is hatched with oblique lines, and the external force detectors 60 that is not used for the comparison by the analyzer 85 is not hatched. In this way, the analyzer 85 analyzes the maximum force quantity among the force quantities of the external forces in a first direction (counterclockwise direction or clockwise direction) around the central axis that are detected by the external force detectors 60, respectively. The analyzer 85 compares each of the maximum force quantity and a force quantity of an external force in a second direction (clockwise direction or counterclockwise direction) opposite to the first direction at the arrangement position of the external force detector 60 that has calculated the maximum force quantity, with the reference value. The analyzer 85 compares the force quantities LAF and RAF at one location with the reference value. An arrangement position where a maximum force quantity has been calculated corresponds to a location that exhibits a maximum value of the reaction force as the main factor for causing an operator to feel the resistance. The reason for making a comparison using the force quantities at such an arrangement position is that when the flexible tube 35 is twisted in each of the counterclockwise direction and the clockwise direction, this arrangement position is presumed to exhibit the most significant difference between the force quantity LAF in the counterclockwise direction and the force quantity RAF in the clockwise direction.

The analyzer 85 need not be limited to analyze the maximum force quantity. For example, the analyzer 85 may analyze an N-th force quantity (N is a natural number of one or more) from the maximum force quantity. The analyzer 85 may compare each of the N-th force quantity and a force quantity of an external force in the direction opposite to the first direction at the arrangement position of the external force detector 60 that has calculated the N-th force quantity, with the reference value. For example, N is set as desired by the input device 170. A maximum value of N is equal to the number of the external force detectors 60. Examples A and B in which a force quantity other than the maximum force quantity is used for the analysis and the comparison will be briefly described. As the example A, if the maximum value of the force quantity is a value that is not related to the twisting (for example, noise, etc.), a maximum value (for example, an N-th value) that is not affected by noise, etc., is used for the analysis and the comparison. As the example B, if the compared force quantities LAF and RAF at the arrangement position in which the maximum force quantity has been calculated are equal to each other, the comparison and the analysis are performed for the force quantities LAF and RAF at the arrangement position in which the next largest force quantity has been calculated.

Alternatively, for example, the analyzer 85 analyzes a portion at which a difference between a force quantity before the twisting and a force quantity after the twisting is greatest, among the force quantities in the first direction around the central axis detected by the external force detectors 60, respectively. The analyzer 85 may compare each of the force quantity LAF of the external force in the counterclockwise direction and the force quantity RAF of the external force in the clockwise direction at the portion at which the difference is greatest, with the reference value, respectively.

Figure 3D:
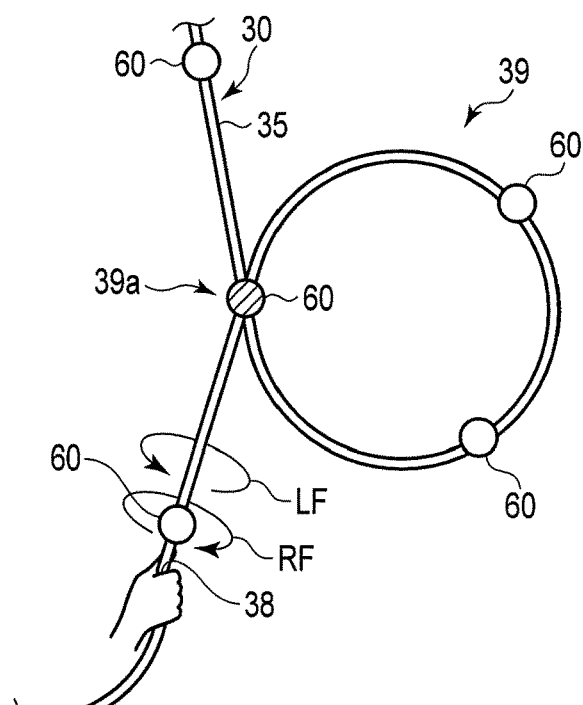
FIG. 3D is a diagram showing an example of an arrangement position of the external force detectors.

As shown in FIG. 3D, as the example 4, the external force detectors 60 are, for example, disposed to be spaced apart from each other at substantially equidistant intervals. For example, the external force detectors 60 are disposed within a range from the distal end section of the flexible tube 35 to the gripped portion 38. The external force detectors 60 calculate the force quantities LAF and RAF at their arrangement positions, respectively. For example, the analyzer 85 extracts, from the calculated force quantities LAF and RAF, the force quantity LAF of the external force RF and the force quantity RAF of the external force RF that are calculated by the external force detector 60 that is disposed at the position where a reaction force is generated by the twisting (for example, the periphery of the intersecting portion 39a). The analyzer 85 then compares each of the force quantity LAF of the external force RF and the force quantity RAF of the external force RF that have been extracted, with the reference value. In FIG. 3D, the external force detector 60 that is used for the comparison by the analyzer 85 is hatched with oblique lines, and the external force detectors 60 that is not used for the comparison by the analyzer 85 is not hatched. The analyzer 85 compares the force quantities LAF and RAF at the position with the reference value. Among the external force detectors 60, the external force detector 60 disposed in the periphery of the intersecting portion 39a may be determined by the shape information. Therefore, the analyzer 85 may analyze the force quantities LAF and RFA detected by the determined external force detector 60.

Figure 3E:
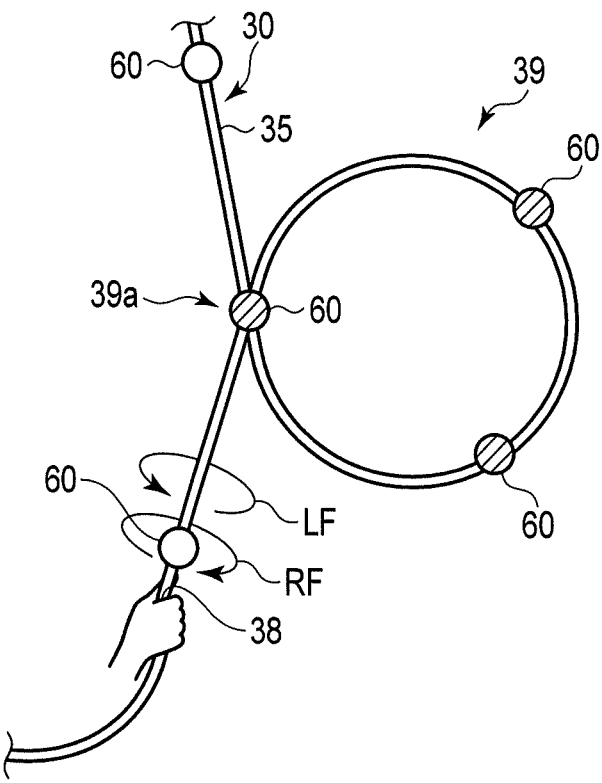
FIG. 3E is a diagram showing an example of an arrangement position of the external force detectors.

As shown in FIG. 3E, as the example 5, for example, the external force detectors 60 are disposed to be spaced apart from each other at substantially equidistant intervals. For example, the external force detectors 60 are disposed within a range from the distal end section of the flexible tube 35 to the gripped portion 38. The external force detectors 60 calculate the force quantities LAF and RAF at their arrangement positions, respectively. For example, the analyzer 85 compares each of a total sum of the force quantities LAFs respectively calculated by the external force detectors 60 disposed within a desired range and a total sum of the force quantities RAFs respectively calculated by the external force detectors 60 disposed within the desired range, with the reference value. In FIG. 3E, the external force detector 60 that is used for the comparison by the analyzer 85 is hatched with oblique lines, and the external force detectors 60 that is not used for the comparison by the analyzer 85 is not hatched. In this way, the analyzer 85 compares each of the total value of the force quantities LAFs at positions within the desired range and the total value of the force quantities RAFs at the positions within the desired range, with the reference value. The desired range is set by the input device 170, for example. The desired range may be set as desired depending on a patient, an operator, etc. The desired range indicates, for example, the loop section 39.

In the examples 3 to 5, the external force detectors 60 are disposed to be spaced apart from each other at substantially equidistant intervals; however, the arrangement is not limited to this way. Intervals between the external force detectors 60 may be adjusted as desired. For example, referring to the distal end section of the flexible tube 35, the gripped portion 38, and a central portion between the distal end section of the flexible tube 35 and the gripped portion 38, the external force detectors 60 may disposed at narrower intervals as extending from the distal end section to the central portion, or may be disposed at narrower intervals as extending from the gripped portion 38 to the central portion. That is, more external force detectors 60 are disposed on a part closer to the central portion and less external force detectors 60 are disposed on a part closer to the distal end section of the flexible tube 35 and a part closer to the gripped portion 38.

Next, the examples 1 to 3 of the reference value that is used by the analyzer 85 for the comparison will be briefly described.

In the example 1, the reference value is manually set by an operator. In the example 2, the reference value is calculated based on a calculation condition freely set in advance by an operator based on force quantities that are accumulated at operator's discretion among the force quantities calculated by the external force detectors 60. In the example 3, the reference value is calculated based on a calculation condition freely set in advance by an operator based on force quantities that are accumulated based on an accumulation condition freely set in advance by an operator among the force quantities calculated by the external force detectors 60. The examples 1 to 3 of the reference value will be described in detail.

First, the example 1 of the reference value will be described.

Figure 5A:
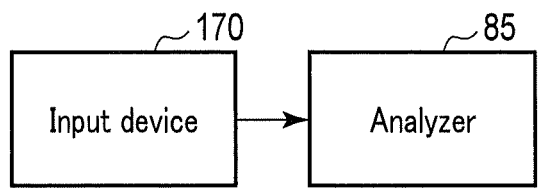
FIG. 5A is a diagram showing an example of a constitution of inputting a reference value to the analyzer.

As the example 1, the reference value is a value freely set by an operator. As shown in FIG. 5A, for example, the reference value is set by an operator with the input device 170 based on his or her experimental rule on a twisting operation or force quantity information to be described later. The set reference value is input to the analyzer 85 through the input device 170. In the example 1, the input device 170 functions as an input section configured to input the reference value as a freely-set value to the analyzer 85.

Figure 6A:
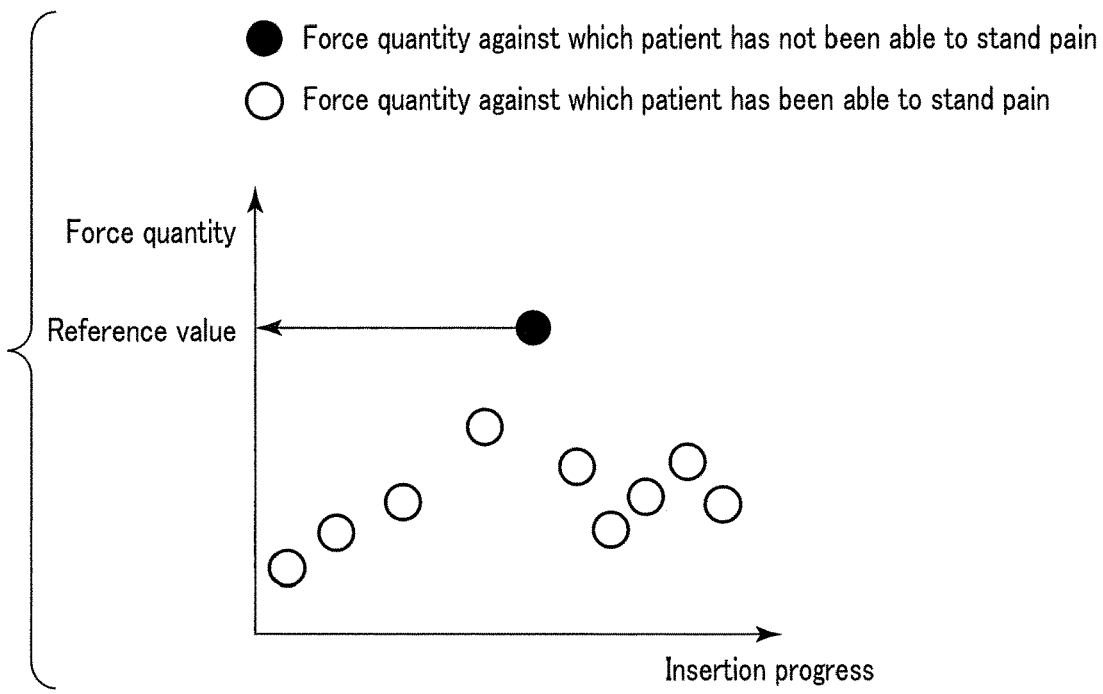
FIG. 6A is a diagram showing an example of setting the reference value.

As shown in FIG. 6A, the force quantity information indicates a relation between a progress of inserting the insertion section 30 into a subject and force quantities calculated by the respective external force detectors 60 in the progress of insertion. The force quantities include a force quantity against which a patient has made some pain complaints, etc., and has not been able to stand the pain, and a force quantity against which the patient has made few pain complaints, etc., and has been able to stand the pain. Among these force quantities, the force quantity against which a patient has made some pain complaints, etc., and has not been able to stand the pain is set as the reference value. The reference value for a pain complaint, etc., may be based on a patient's voice, pulse, movement, etc., during the insertion operation.

Herein, the analyzer 85 analyzes force quantities calculated by the respective external force detectors 60 in the progress of insertion, for example. The generation section 87 generates force quantity information based on an analysis result. The force quantity information is output to the providing device 150 through the output section 89. The force quantity information is displayed on the providing device 150 when the reference value is set, for example. For example, an operator sets the reference value by visually checking force quantity information displayed on the providing device 150 and a patient, and performing operation with, for example, the button 40b of the control section 40 or the input device 170.

Next, a common constitution between the examples 2 and 3 of the reference value will be described.

For the examples 2 and 3 of the reference value, as shown in FIG. 5B, the insertion apparatus 10 has a storage section 91 configured to store all force quantities LAFs and RAFs calculated by the external force detectors 60, and an accumulation section 93 configured to accumulate one or more force quantities from the force quantities LAFs and RAFs stored in the storage section 91. The insertion apparatus 10 has the reference value calculator 95 configured to calculate the reference value based on accumulated force quantities, and an input section 97 configured to input the calculated reference value to the analyzer 85. The storage section 91, the accumulation section 93, the reference value calculator 95, and the input section 97 are disposed on the control device 80.

For example, the accumulation section 93 has a memory or a storage. At least one of the reference value calculator 95 and the input section 97 may be constituted by a processor. In the case where at least one of the reference value calculator 95 and the input section 97 is constituted by a processor, an internal or an external memory (not shown) accessible by a computer is disposed. The internal memory or external memory stores a program code to be executed by the processor such that the processor is caused to function as at least one of the reference value calculator 95 and the input section 97.

Next, the example 2 of the reference value will be described.

In the example 2 of the reference value, the input device 170 functions as a selection setting section configured to output an instruction to the accumulation section 93, and to select a force quantity to be accumulated in the accumulation section, from the force quantities LAFs and RAFs stored in the storage section 91. The accumulation section 93 accumulates the force quantity selected by the selection setting section from the force quantities stored in the storage section 91. The accumulation section 93 constantly accumulates the selected force quantity as a candidate for an optimal reference value.

As the example 1 of selection for the accumulation, the selection indicates a discretionary determination for an operator after the completion of examination (twisting operation), based on whether the loop section has been eliminated or not, a patient's complaint about pain caused by the twisting operation, etc. The operator performs the selection by visually checking the providing device 150 displaying the force quantities stored in the storage section 91 to make selection operation with the input device 170.

As the example 2 of selection for the accumulation, the selection indicates a discretionary determination for an operator who has confirmed a condition of a patient in the progress of inserting the insertion section 30 into a subject. In this case, the operator determines a force quantity against which the patient has made few pain complaints, etc., and has been able to stand the pain in the progress of insertion. Then, a force quantity determined by the operator is accumulated in the accumulation section 93. The reference value for the pain complaint, etc., may be based on a patient's voice, pulse, movement, etc., during the insertion operation. For example, the operator sets the reference value by visually checking force quantity information displayed on the providing device 150 and the patient, and performing operation with, for example, the button 40b of the control section 40 or the input device 170.

In the example 2 of the reference value, the input device 170 functions as a selection setting section configured to set and input in advance a calculation condition set by an operator to the reference value calculator 95. The calculation condition includes, for example, a first condition and a second condition. The operator sets which one of the first condition and the second condition to use.

The first condition of the calculation condition indicates, for example, that a force quantity among the accumulated force quantities that is optimal for patient information is used as the reference value. Patient information includes a patient's sex, age, preexisting disorder, surgical history, current condition, etc. Patient information is only required to be stored in the storage section 91, for example. For example, an operator sets the reference value by visually checking patient information displayed on the providing device 150 and force quantities accumulated in the accumulation section 93, and performing operation with, for example, the button 40b of the control section 40 or the input device 170.

Hereinafter, an example of selecting the reference value from the force quantities will be described.

With respect to a patient subjected to multiple examinations, an operator selects a force quantity against which the patient has not been able to stand the pain, from force quantities used in the previous examinations, and set this selected force quantity as the reference value, using the button 60b or the input device 170.

Alternatively, the operator visually checks the providing device 150 and selects, from stored patient information on patients, patient information that is most similar to patient information on a patient who is about to be examined, by using the button 40b or the input device 170. The operator sets, as the reference value, the force quantity that is optimal for the selected patient information. The optimal force quantity indicates, for example, a force quantity against which a patient has not been able to stand the pain.

Figure 6B:
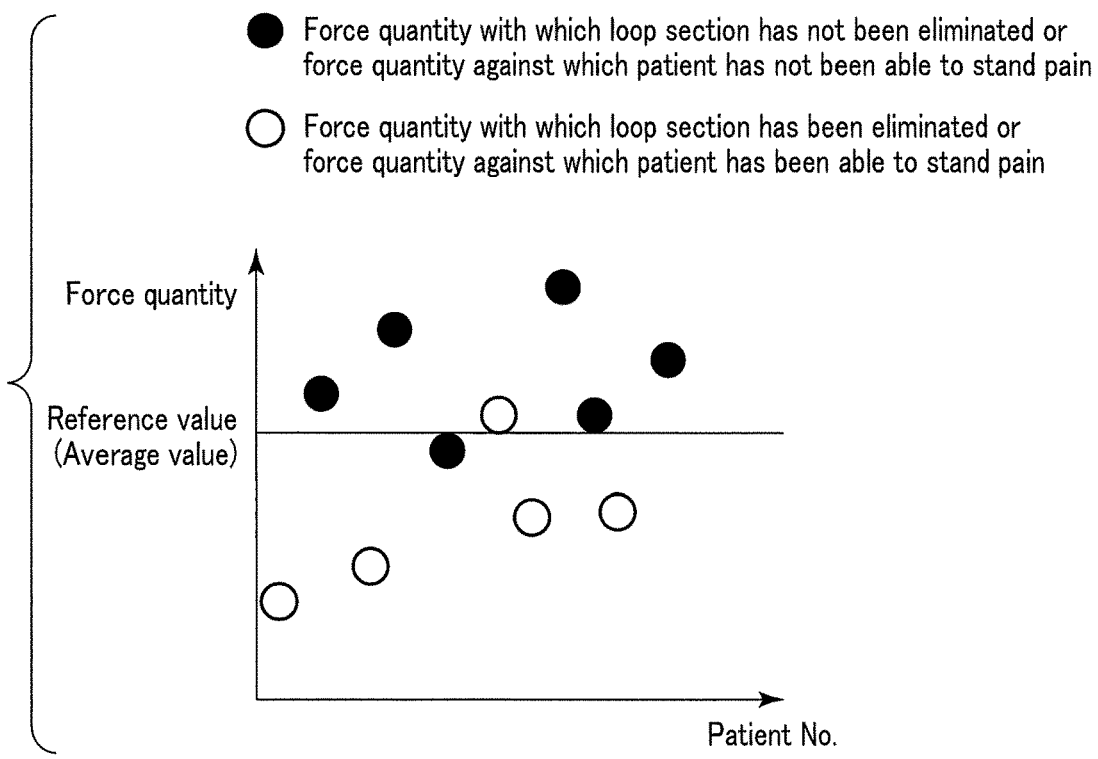
FIG. 6B is a diagram showing an example of setting the reference value.
Figure 6C:
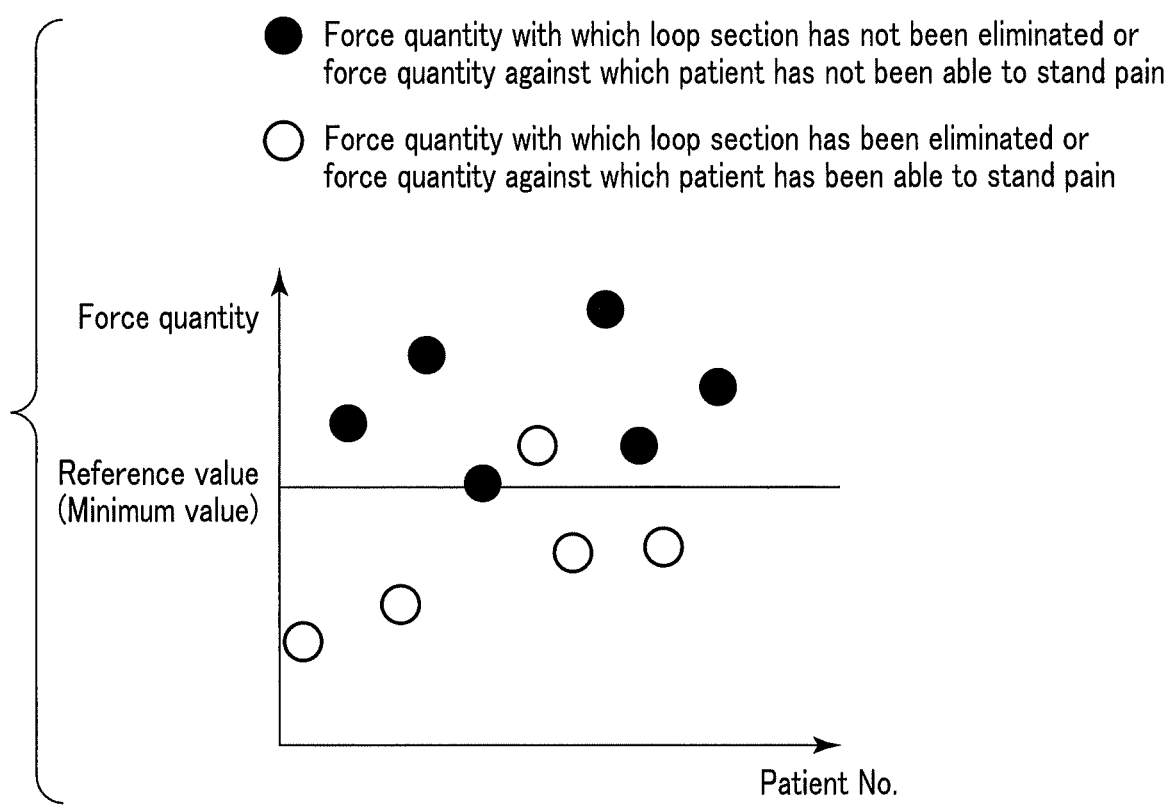
FIG. 6C is a diagram showing an example of setting the reference value.
Figure 6D:
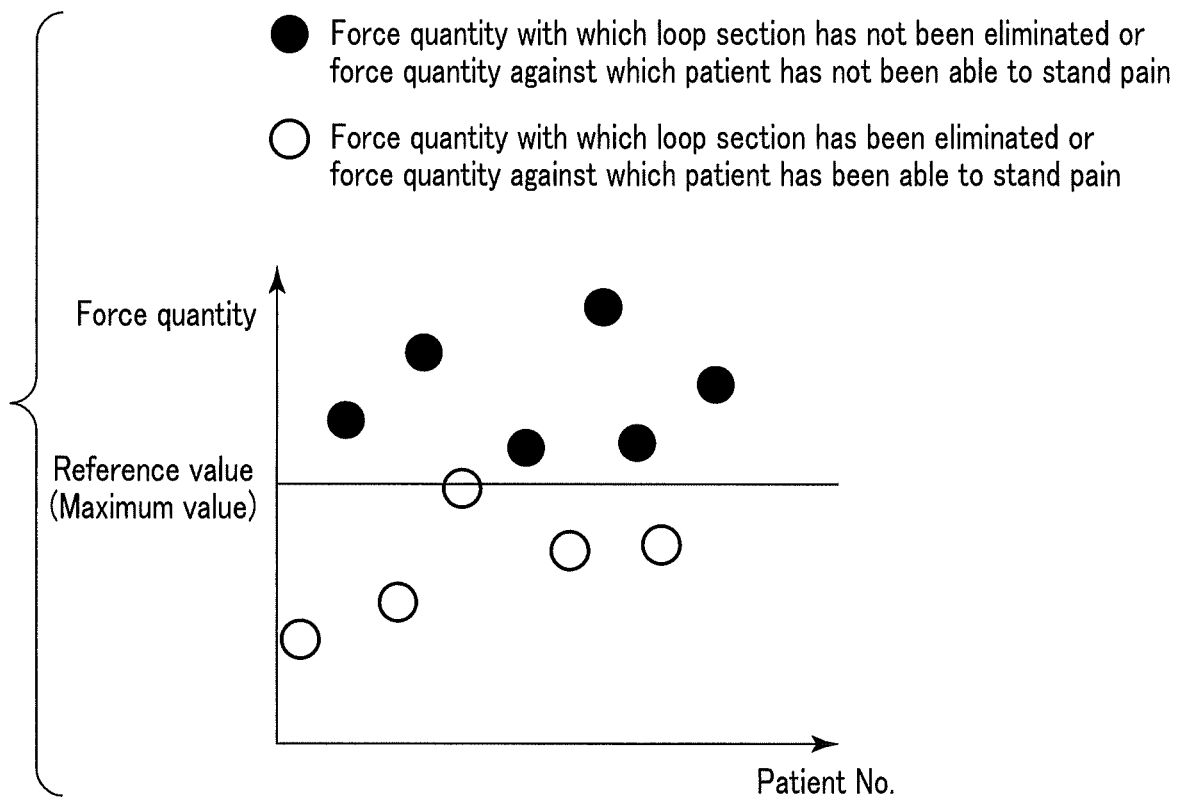
FIG. 6D is a diagram showing an example of setting the reference value.

The second condition of the calculation condition indicates that, as shown in FIGS. 6B, 6C, and 6D, for example, any one of an average force quantity, a minimum force quantity, and a maximum force quantity of the accumulated force quantities is used as the reference value. The accumulated force quantities indicate, for example, any one of a force quantity with which the loop section has not been eliminated, a force quantity with which the loop section has been eliminated, a force quantity against which a patient has made some pain complaints and has not been able to stand the pain, and a force quantity against which the patient has made few pain complaints and has been able to stand the pain. As shown in FIG. 6C, the minimum force quantity indicates the smallest force quantity among force quantities that are included in the accumulated force quantities and with which the loop section has not been eliminated or against which a patient has not been able to stand the pain caused by a twisting operation. As shown in FIG. 6D, the maximum force quantity indicates the greatest force quantity among force quantities that are included in the accumulated force quantities and with which the loop section has been eliminated or against which a patient has been able to stand the pain caused by a twisting operation.

As the reference value, the reference value calculator 95 does not necessarily calculate force quantities corresponding to the first condition and the second condition with no change. As the reference value, for example, the reference value calculator 95 may calculate an integral value obtained by integrating a force quantity corresponding to the first and second conditions over a period in time such as a twisting time period.

As described above, the reference value calculator 95 calculates a force quantity corresponding to the calculation condition input to the reference value calculator 95 among the force quantities accumulated in the accumulation section 93.

The input section 97 inputs, as the reference value, the force quantity calculated by the reference value calculator 95 to the analyzer 85.

The input device 170 may set, as the reference value, a force quantity among the force quantities accumulated in the accumulation section 93, while omitting the reference value calculator 95 and the input section 97. This setting is performed (determined) by, for example, the operator. The operator sets a force quantity with the input device 170 by referring to the providing device 150 displaying the force quantities accumulated in the accumulation section 93. For example, the force quantity to be set may be any one of an average force quantity, a maximum force quantity, and a minimum force quantity. The input device 170 inputs the set force quantity as the reference value to the analyzer 85.

Next, the example 3 of the reference value will be described.

In the example 3 of the reference value, the input device 170 functions as a selection setting section configured to set in advance, in the accumulation section 93, an accumulation condition for the accumulation section 93 set by an operator. The accumulation section 93 accumulates a force quantity among the force quantities LAFs and RAFs stored in the storage section 91, based on the accumulation condition set in advance in the accumulation section 93. The accumulation condition includes, for example, a first condition, a second condition, and a third condition.

The first condition of the accumulation condition is an instruction to accumulate all the force quantities LAFs and RAFs stored in the storage section 91.

The second condition of the accumulation condition is a condition indicating that a force quantity with which the loop section has been eliminated or a force quantity with which the loop section has not been eliminated among the force quantities LAFs and RAFs stored in the storage section 91 is accumulated. The force quantity with which the loop section has been eliminated indicates, for example, a force quantity with which the flexible tube 35 has been brought into a substantially linear state by the twisting operation. A state of the flexible tube 35 may be determined by the analyzer 85 based on shape information of the flexible tube 35 calculated by the state calculator 81. A maximum value of the force quantity with which the loop section has been eliminated may be utilized as the reference value. A minimum value of the force quantity with which the loop section has not been eliminated may be utilized as the reference value.

The third condition of the accumulation condition is a condition indicating that force quantities among the force quantities LAFs and RAFs stored in the storage section 91 are accumulated based on a patient's condition. These force quantities indicate a force quantity against which a patient has made few pain complaints, etc., and has been able to stand the pain, and a force quantity against which the patient has made some pain complaints, etc., and has not been able to stand the pain. The reference value for a pain complaint, etc., may be set in advance by an operator based on a patient's voice, pulse, movement, etc., during the insertion operation, and stored in the accumulation section 93. A maximum value of the force quantity against which a patient has been able to stand the pain may be utilized as the reference value. A minimum value of the force quantity against which a patient has not been able to stand the pain may be utilized as the reference value.

In the example 3 of the reference value, as in the example 2 of the reference value, the input device 170 functions as a selection setting section configured to set and input in advance a calculation condition set by an operator to the reference value calculator 95. The reference value calculator 95 calculates the reference value based on a force quantity corresponding to a calculation condition input to the reference value calculator 95 among the accumulated force quantities. A calculation condition herein is similar to the calculation condition described in the example 2 of the reference value.

The input section 97 inputs, as the reference value, the force quantity calculated by the reference value calculator 95 to the analyzer 85.

In the examples 2 and 3 of the reference value, the input device 170 may set a correction value for the reference value. The correction value is based on patient information on a patient as a subject into which the flexible tube 35 is to be inserted, and model information of the insertion apparatus 10. Model information includes, for example, a length, a thickness, and a hardness of the flexible tube 35. Model information is only required to be stored in the storage section 91, for example.

Next, a force quantity calculated by the external force detector 60, a force quantity analyzed by the analyzer 85, a force quantity accumulated in the accumulation section 93, and a force quantity used as the reference value will be specifically described below. As these force quantities, a force quantity or a value described below may be used.

For example, the force quantity may be a force quantity at the time when the application of a quantity of twisting to the flexible tube 35 is completed. The force quantity may be a maximum force quantity during a period in time from the start to the completion of application of a given quantity of twisting to the flexible tube 35. The value may be a value obtained by integrating a force quantity from the start to the completion of application of a given quantity of twisting to the flexible tube 35. The value may be a value obtained by integrating a maximum force quantity during a period from the start to the completion of application of a given quantity of twisting to the flexible tube 35, over a period in time from before to after a point in time when the maximum force quantity is calculated. For example, each of plots shown in FIG. 6B may be a force quantity at the time when the application of twisting with a given quantity to the flexible tube 35 is completed, or a maximum force quantity during a period from the start to the completion of application.

Next, the generation section 87, the output section 89, and the providing device 150 will be described.

The generation section 87 shown in FIG. 2 generates the first propriety information regarding the current propriety of a twisting operation with respect to the flexible tube 35, depending on an analysis result (comparison result) by the analyzer 85. The first propriety information indicates whether or not to permit the twisting operation in the current situation. Thus, the first propriety information includes, for example, first warning information regarding warning against the twisting operation in the current situation, and first permission information regarding permission for the twisting operation in the current situation. For example, the first warning information indicates that the twisting operation is not permitted and the elimination of the loop section is impossible. For example, the first warning information indicates that the twisting operation is permitted and the elimination of the loop section is possible.

The generation section 87 generates the first propriety information in accordance with the determination result (comparison result) by the analyzer 85. When the analyzer 85 analyzes that both of the two force quantities LAF and RAF are larger than the reference value, the generation section 87 generates the first warning information of the first propriety information. When the analyzer 85 analyzes that at least one of the two force quantities LAF and RAF is smaller than the reference value, the generation information generates the first permission information of the first propriety information.

As described above, the generation section 87 generates, as the first propriety information, warning, or permission with respect to the twisting operation with which the loop section is eliminated and the flexible tube 35 is changed into a substantially linear state. In practice, the first propriety information described above functions as support information for an operation of eliminating the loop section to change the flexible tube 35 into a substantially linear state.

The generation section 87 outputs the generated first propriety information to the output section 89.

The output section 89 outputs the first propriety information generated by the generation section 87 to the providing device 150.

The providing device 150 provides the first propriety information as information including at least one of characters 155*a* (see FIG. 7A), a symbol 155*b* (see FIG. 7B), light emission (see FIGS. 7C and 7D), sound 155*h* (see FIGS. 1 and 7E), fragrance, and vibration. The first propriety information will be briefly described below.

The providing device 150 may provide the first propriety information as a display to the monitor. A position of the display may not particularly limited, as long as an operator can visually check the display. As a result, the first propriety information may be displayed overlapping the image 151 or the image 153, or may be displayed in a different position from the image 151 or the image 153.

As shown in FIG. 7A, the providing device 150 may display the first warning information of the first propriety information, in the form of the characters 155*a* such as "Elimination: NO". Although not shown, the providing device 150 may display the first permission information of the first propriety information, in the form of the characters such as "Elimination: OK".

As shown in FIG. 7B, the providing device 150 may display the first propriety information in the form of the symbol 155*b*.

As shown in FIGS. 7C and 7D, the providing device 150 may provide the first propriety information in the form of light emission.

As shown in FIG. 7C, the providing device 150 may have light emitting sections 155*f* disposed on the monitor and configured to emit light. Positions of the light emitting sections 155*f* are not particularly limited, as long as they can be visually checked by an operator. The light emitting sections 155*f* are disposed in different positions from the image 151 or the image 153, for example. The light emitting section 155*f* may be disposed so as to overlap the image 151 or the image 153. The image 151 or the image 153 on the monitor is a separate entity from the light emitting sections 155*f*; however, they may serve as the light emitting sections 155*f*.

As shown in FIG. 7D, the providing device 150 may be disposed on the endoscope 20 and function as a light emitting element 155*g* configured to emit light. For example, light emitting elements 155*g* are disposed on the control section 40. Each of the light emitting elements 155*g* disposed on the control section 40 has, for example, an LED, etc. For example, the light emitting elements 155*g* may be disposed on the gripped portion 38 or an exposed portion of the flexible tube 35, which is disposed outside the pipeline section.

The light emitting sections 155*f* are provided for the first warning information and the first permission information, respectively. Only the light emitting section 155*f* of the first warning information or the first permission information is turned on or caused to blink according to an analysis result by the analyzer 85. When the light emitting section 155*f* for the first warning information is turned on/caused to blink, the light emitting section 155*f* for the first permission information is turned off. When the light emitting section 155*f* for the first permission information is turned on/caused to blink, the light emitting section 155*f* for the first warning information is turned off. A single light emitting section 155*f* may be provided and emit light in a color corresponding to the first warning information or the first permission information. The color corresponding to the first warning information or the first permission information may be input and set in advance as desired with the input device 170, for example. While the description has been made using the light emitting sections 155*f*, this content is also applicable to the light emitting elements 155*g*.

Figure 7E:
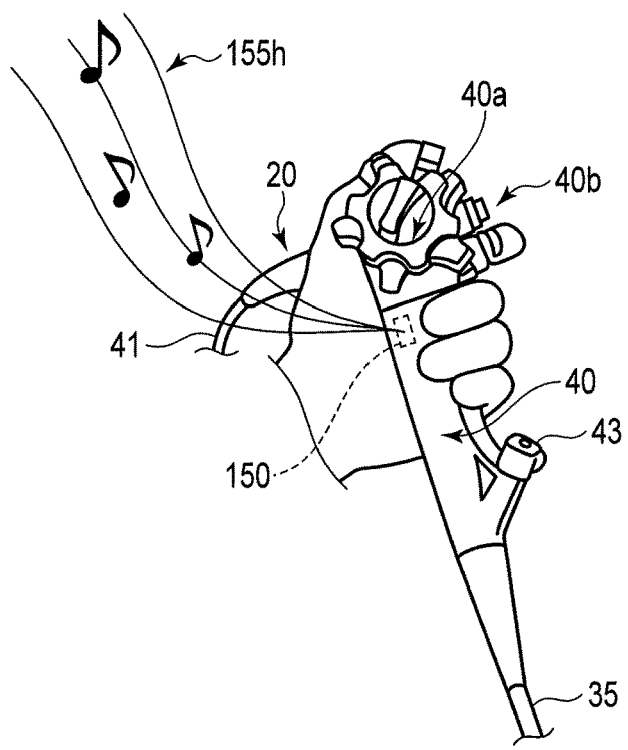
FIG. 7E shows an example of providing propriety information.

As shown in FIGS. 1 and 7E, the providing device 150 may output the sound 155*h* corresponding to the first propriety information (the first warning information or the first permission information). The sound 155*h* corresponding to the first propriety information (the first warning information or the first permission information) may be input and set in advance as desired with the input device 170, for example. The sound 155*h* includes, for example, voice, tone color, etc. For example, the providing device 150 may be disposed inside the control device 80 or inside the control section 40. The providing device 150 functions as a sound source or a speaker. For example, the providing device 150 may be disposed in a room, etc., in which the insertion apparatus 10 is disposed.

Although not shown, the providing device 150 may output fragrance corresponding to the first propriety information (the first warning information or the first permission information). For example, the providing device 150 is disposed in the control device 80, the control section 40, a room in which the insertion apparatus 10 is disposed, or the like. Although not shown, the providing device 150 may output the vibration corresponding to the first propriety information (the first warning information or the first permission information). For example, the providing device 150 is disposed in the control device 80 or the control section 40.

It is assumed that the twisting operation for eliminating the loop section and changing the flexible tube into a substantially linear state is performed when the generation section 87 generates the first permission information of the first propriety information or when the providing device 150 provides the first permission information of the first propriety information. Herein, for example, it is assumed that a right twisting operation in the clockwise direction is performed.

Figure 7F:
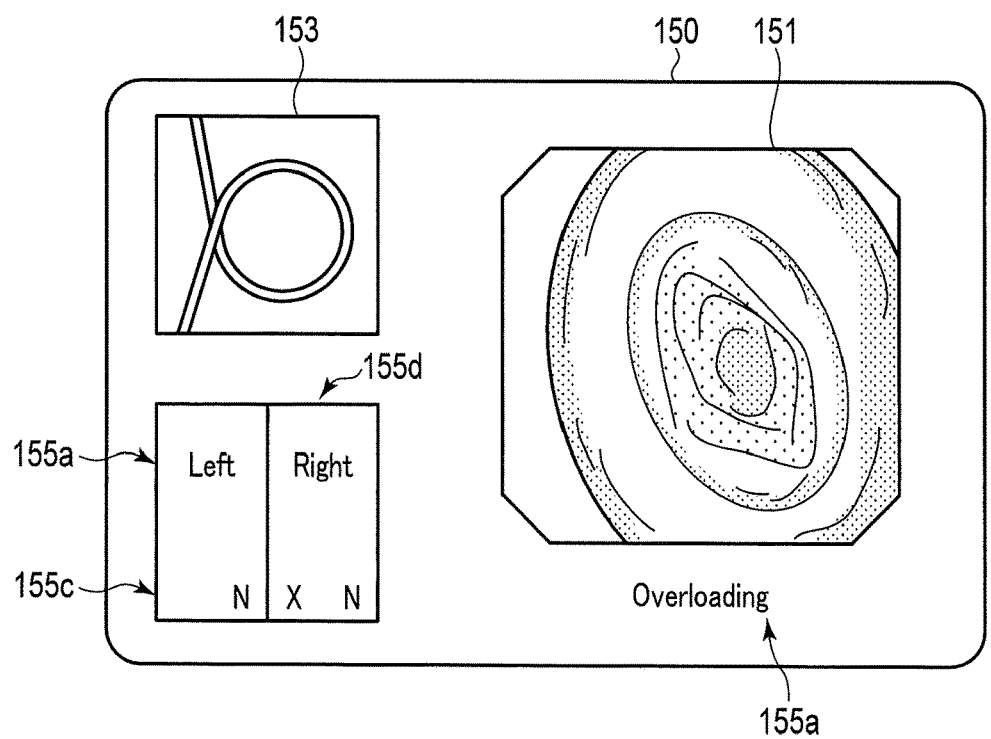
FIG. 7F shows an example of providing propriety information.

The external force detector 60 calculates the force quantity RAF and outputs the calculated force quantity RAF to the output section 89. The output section 89 outputs this force quantity RAF to the providing device 150. As shown in FIG. 7F, the providing device 150 displays this force quantity RAF in the form of the characters 155a indicating the twisting direction in the twisting operation and a numerical value 155c of the force quantity RAF (unit: N (newton)). The numerical value 155c indicates an operator's twisting force applied from his or her one hand to the hand side of the flexible tube 35 during the twisting operation being performed. A numerical value may be calculated by the force quantity calculator 61b based on the force quantity RAF. FIG. 7F shows an example of a display area 155d that displays the characters 155a and the numerical values 155c. A right area of the display area 155d displays "Right", which is the characters 155a indicating the twisting direction, and displays X N, which is the numerical value 155c. In this case, a left area of the display area 155d displays "Left", which is the characters 155a indicating the twisting direction, while the numerical value 155c indicates an empty field. In this case, the left area of the display area 155d may not be displayed.

A twisting direction is analyzed by the analyzer 85 based on a force quantity calculated by the external force detector 60.

The external force detector 60 outputs the calculated force RAF to the analyzer 85.

The analyzer 85 analyzes the force quantity RAF and the reference value. The reference value herein is the same as that in the examples 1 to 3 of the reference value used by the analyzer 85 for the comparison. Therefore, the description about the reference value is omitted herein. As an example of analysis, the analyzer 85 compares the force quantity RAF with the reference value. The analyzer 85 determines whether or not the force quantity RAF is larger than the reference value. The analyzer 85 outputs the determination result (comparison result) to the generation section 87.

The generation section 87 generates the second propriety information in accordance with an analysis result (comparison result) by the analyzer 85. The second propriety information indicates whether an excessive quantity of force is applied or not to the flexible tube 35 while the twisting operation is performed in order to eliminate the loop section formed in the flexible tube 35 and in order to change the flexible tube 35 into a substantially linear state. This application results in a rapid change in shape of the flexible tube and rapid elimination of the loop section, which overloads a patient and brings about a pain on him or her. Therefore, the second propriety information indicates whether or not a force quantity in the twisting operation is appropriate. For example, the second propriety information may include second warning information regarding warning against a force quantity used in the twisting operation, and second permission information regarding permission for a force quantity used in the twisting operation. For example, the second warning information indicates that: the twisting operation using this force quantity is not permitted; the twisting operation may cause a patient pain; a patient makes some pain complains, etc., and cannot stand the pain; and the twisting operation is causing a patient pain. For example, the second permission information indicates that: the twisting operation using this force quantity is permitted; the twisting operation does not cause a patient pain; and a patient makes few pain complains, etc., and can stand the pain. The second permission information indicates that the loop section can be eliminated under a condition that a patient is given no pain or can stand the pain.

The generation section 87 generates the second propriety information in accordance with the analysis result (comparison result) by the analyzer 85. When the analyzer 85 analyses that the force quantity RAF is larger than the reference value, the generation section 87 generates the second warning information of the second propriety information. When the analyzer 85 analyses that the force quantity RAF is smaller than the reference value, the generation section 87 generates the second permission information of the second propriety information.

The generation section 87 outputs the generated second propriety information to the output section 89.

The output section 89 outputs the second propriety information generated by the generation section 87 to the providing device 150.

As shown in FIG. 7F, the providing device 150 may display the second warning information of the second propriety information, in the form of the characters 155a such as "Overloading". Although not shown, the providing device 150 may display the second permission information of the second propriety information, in the form of the characters such as "Not Overloading (Appropriate Force Amount)".

Although not shown, the providing device 150 provides the second propriety information as information including at least one of the characters 155a (see FIG. 7A), the symbol 155b (see FIG. 7B), the numerical value 155c of the force quantity (FIG. 7F), light emission (see FIGS. 7C and 7D), the sound 155h (see FIGS. 1 and 7E), fragrance, and vibration, in a similar manner to the first propriety information.

A method of operating the insertion apparatus 10 will be described with reference to FIGS. 8A, 8B, 9A, 9B, and 9C.

Figure 8A:
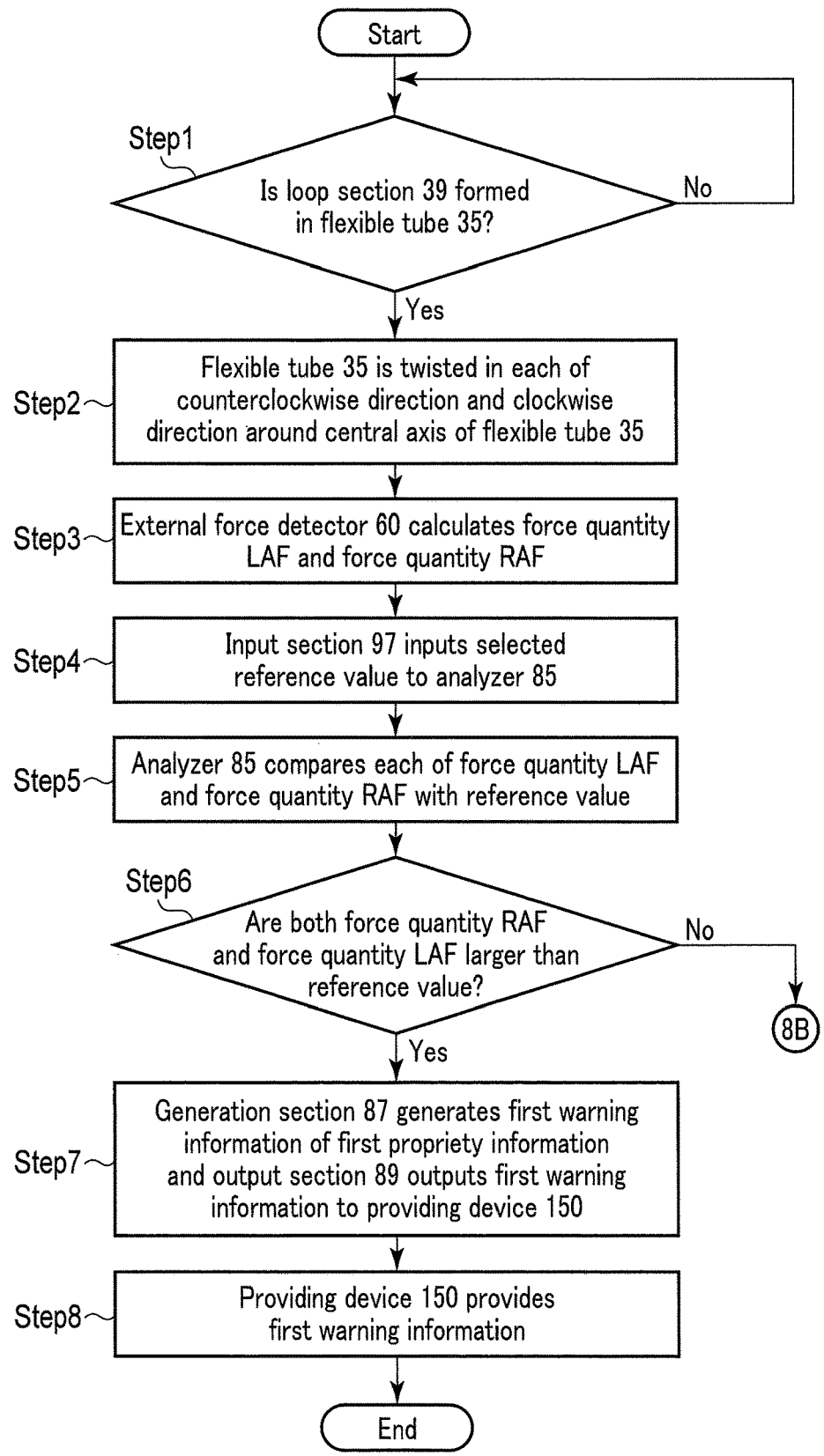
FIG. 8A is a part of flowchart showing an operation method of the flexible tube insertion apparatus.

As shown in FIG. 8A, when a push-operation of the flexible tube 35 is performed and the flexible tube 35 advances toward a deep part of a large intestine along an intestine wall of the large intestine, the state detector 50 detects the state information of the flexible tube 35 and the state calculator 81 calculates shape information of the flexible tube 35 based on the state information. The shape information is displayed as a bent shape of the flexible tube 35 on the monitor of the providing device 150. The shape information is displayed on the monitor in the form of the image 153.

An operator visually checks the monitor to determine whether or not the loop section 39 is formed in the flexible tube 35 (Step 1). The formation of the loop section 39 may be determined by the operator based on the sensation felt by the operator's hand gripping the hand side of the flexible tube 35 when the operator pushes the flexible tube 35 toward the deep part.

If the loop section 39 is not formed (Step 1: No), the push-operation of the flexible tube 35 is continuously performed, and the operation returns to Step 1.

If the loop section 39 is formed (Step 1: Yes), the push-operation of the flexible tube 35 is interrupted. The hand side of the flexible tube 35 is twisted in each of the counterclockwise direction and the clockwise direction around the central axis of the flexible tube 35 by the operator's one hand gripping the hand side of the flexible tube 35. As a result, the flexible tube 35 is twisted in the counterclockwise direction and the clockwise direction, respectively, around the central axis of the flexible tube 35 (Step 2). For example, twisting is only required to be performed once in each direction. In such the twisting operation, for example, a left twisting operation in the counterclockwise direction is performed, and after the left twisting operation, a right twisting operation in the clockwise direction is performed. The right twisting operation follows the left twisting operation. The order of the left twisting operation and the right twisting operation is not particularly limited.

The external force detector 60 detects the external force LF in the counterclockwise direction and the external force RF in the clockwise direction, and calculates the force quantity LAF of the external force LF and the force quantity RAF of the external force RF. The external force detector 60 outputs the calculated force quantities LAF and RAF to the analyzer 85 (Step 3).

The input section 97 inputs a selected reference value to the analyzer 85 (Step 4).

Herein, the examples 1 to 3 of an operation method from the selection to the input of the reference value in Step S4 will be described.

Figure 9A:
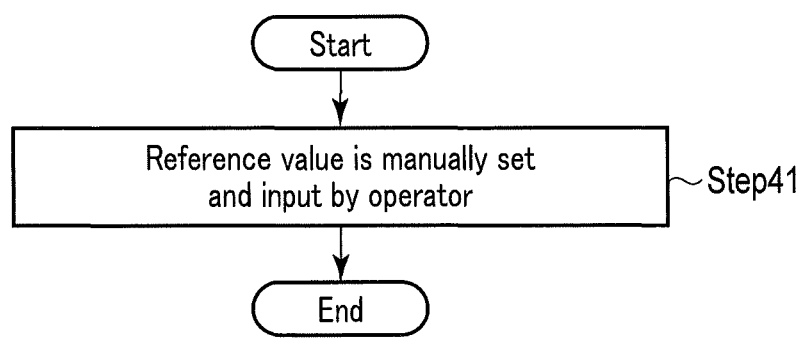
FIG. 9A is a flowchart showing an example 1 of the operation method from selection to input of the reference value.

The example 1 of the operation method may be performed in Step 4 or may be performed in a separate step from the operation flow of the insertion apparatus 10. As the example 1 of the operation method, as shown in FIG. 9A, the reference value as a given value is manually set and input by an operator (Step 41). In Step 41, for example, the operator sets the reference value with the input device 170 based on the operator's experimental rule on the twisting operation or the force quantity information, and inputs the reference value to the analyzer 85 through the input device 170. The operation in Step 4 is then terminated and the operation of the insertion apparatus 10 proceeds to Step 5.

Figure 9B:
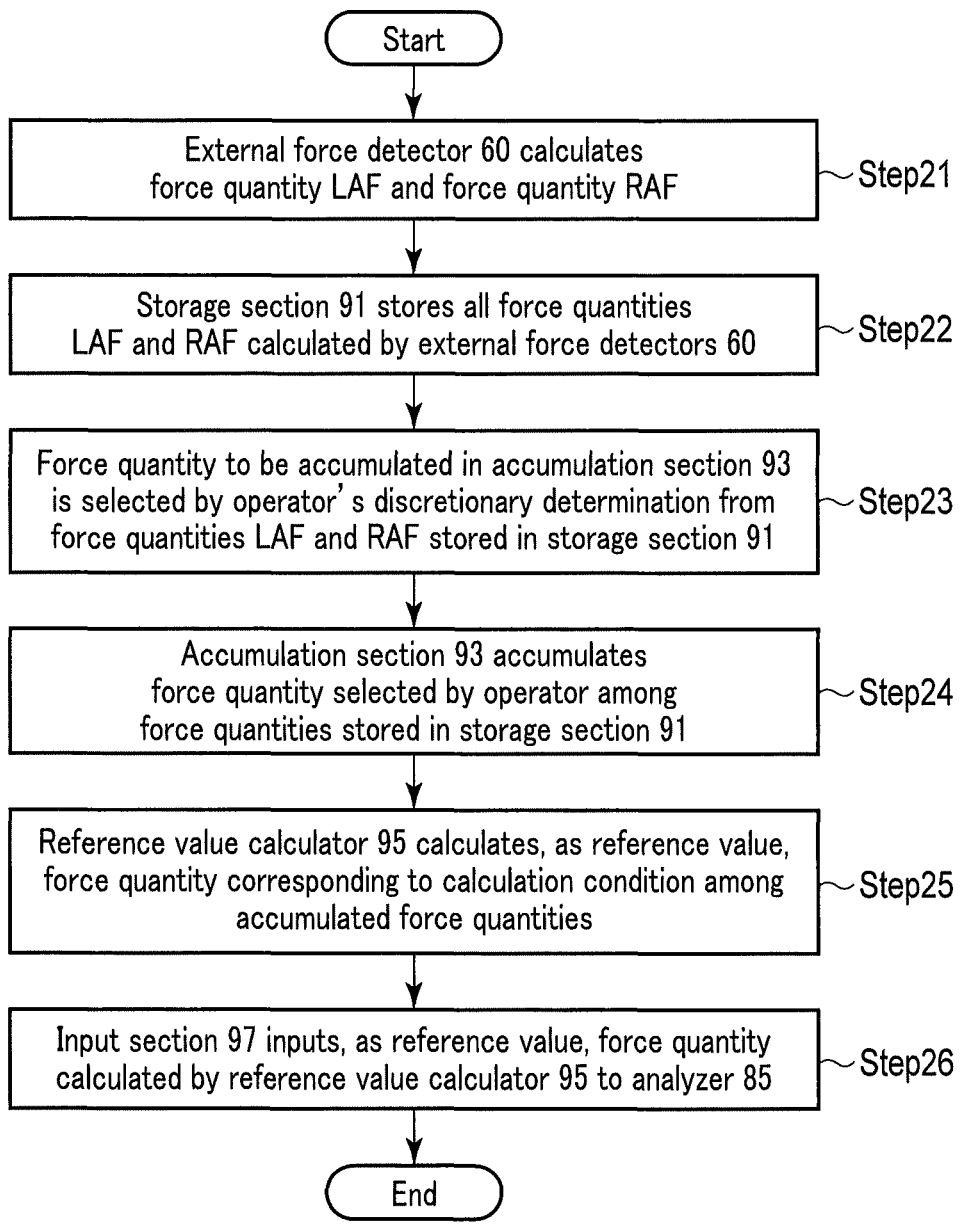
FIG. 9B is a flowchart showing an example 2 of the operation method from selection to input of the reference value.

The example 2 of the operation method is performed in advance in a separate step from the operation flow of the insertion apparatus 10. As the example 2 of the operation method, as shown in FIG. 9B, the external force detector 60 calculates the force quantities LAF and RAF (Step 21). The storage section 91 stores all of the force quantities LAFs and RAFs calculated by the external force detector 60 (Step 22). A force quantity to be accumulated in the accumulation section 93 is selected by the operator's discretionary determination from the force quantities LAFs and RAFs stored in the storage section 91 (Step 23). In Step S23, for example, the operator selects such a force quantity with the input device 170 after the examination, based on whether or not the loop section has been successfully eliminated, a patient's complaint about pain caused by the twisting operation, etc., or by confirming the patient's condition in the progress of insertion.

Next, the accumulation section 93 accumulates the force quantity selected by the operator's discretionary determination among the force quantities stored in the storage section 91 (Step 24). The reference value calculator 95 calculates, as the reference value, the force quantity that is corresponding to a calculation condition set by the operator and included in the accumulated force quantities (Step 25). In Step 25, for example, the operator sets the calculation condition with the input device 170, and inputs the calculation condition to the reference value calculator 95 through the input device 170. The input section 97 inputs, as the reference value, the force quantity calculated by the reference value calculator 95 to the analyzer 85 (Step 26). The operation in Step 4 is terminated and the operation of the insertion apparatus 10 proceeds to Step 5.

Figure 9C:
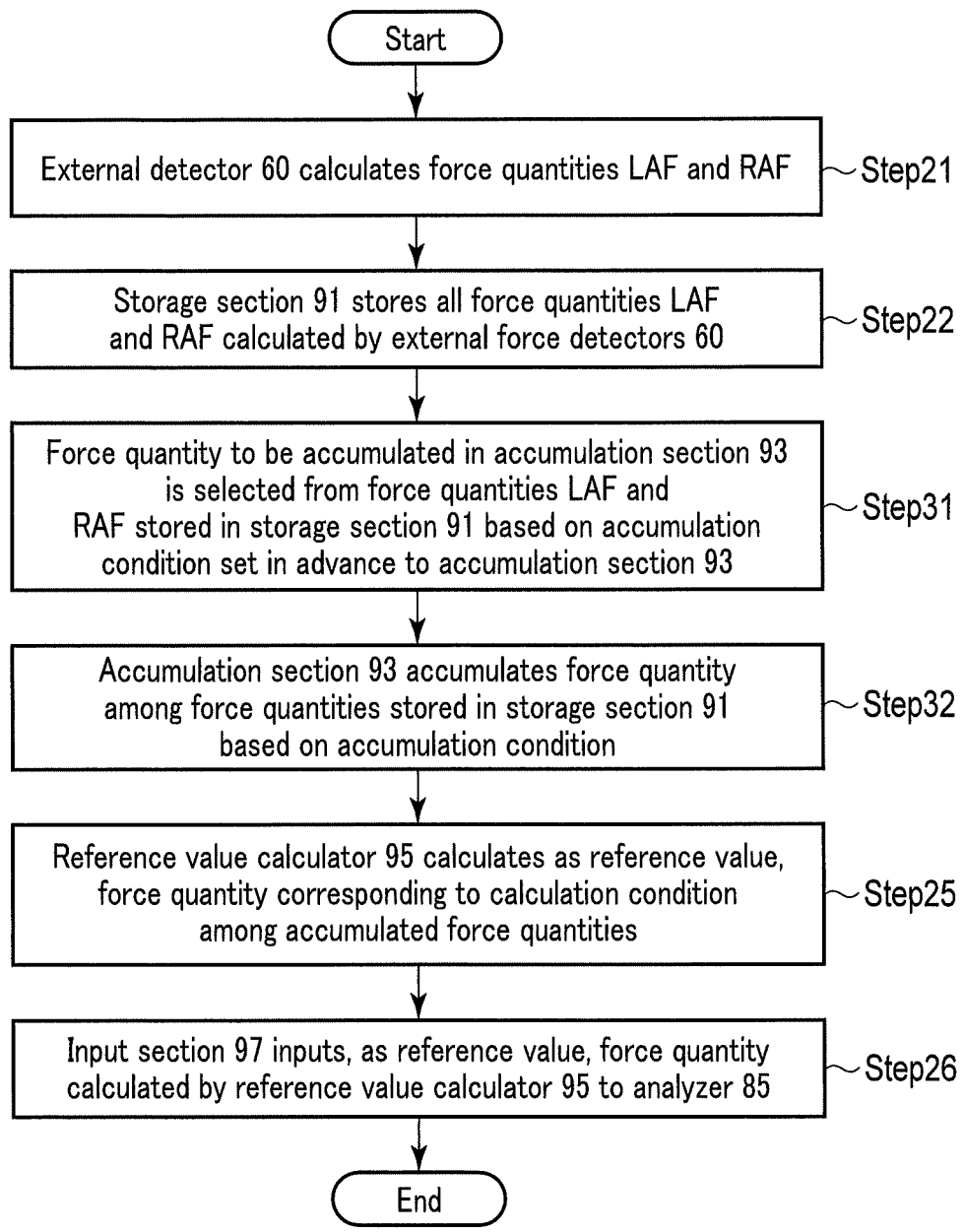
FIG. 9C is a flowchart showing an example 3 of the operation method from selection to input of the reference value.

The example 3 of the operation method is performed in advance in a separate step from the operation flow of the insertion apparatus 10. As the example 3 of the operation method, as shown in FIG. 9C, Steps 21 and 22 are performed in sequence as in the example 2. A force quantity to be accumulated in the accumulation section 93 is selected from the force quantities LAFs and RAFs stored in the storage section 91 based on an accumulation condition set in advance to the accumulation section 93 (Step 31). In Step 31, the operator inputs in advance the accumulation condition set with the input device 170 to the accumulation section 93. The accumulation section 93 accumulates a force quantity among force quantities stored in the storage section 91, based on the accumulation condition set in advance by the operator (Step 32). After Step 32, Steps 25 and 26 are performed in sequence. The operation in Step 4 is terminated and the operation of the insertion apparatus 10 proceeds to Step 5.

Referring back to FIG. 8A, the method of operating the insertion apparatus 10 will be described.

The analyzer 85 compares each of the force quantities LAF and RAF with the reference value (Step 5).

In Steps 3 and 5, the comparison operation by the analyzer 85 differs in accordance with the examples 1 to 5 of an arrangement position of the external force detector 60 shown in FIGS. 3A, 3B, 3C, 3D, and 3E.

The analyzer 85 determines whether or not both of the force quantities LAF and RAF are larger than the reference value, and outputs the determination result to the generation section (Step 6).

For example, if both of the force quantities LAF and RAF are larger than the reference value (Step 6: Yes), the generation section 87 generates the first warning information of the first propriety information, and the output section 89 outputs the first warning information of the first propriety information to the providing device 150 (Step 7). The providing device 150 provides the first warning information of the first propriety information (Step 8). After the first warning information of the first propriety information is provided, the operation is terminated.

Figure 8B:
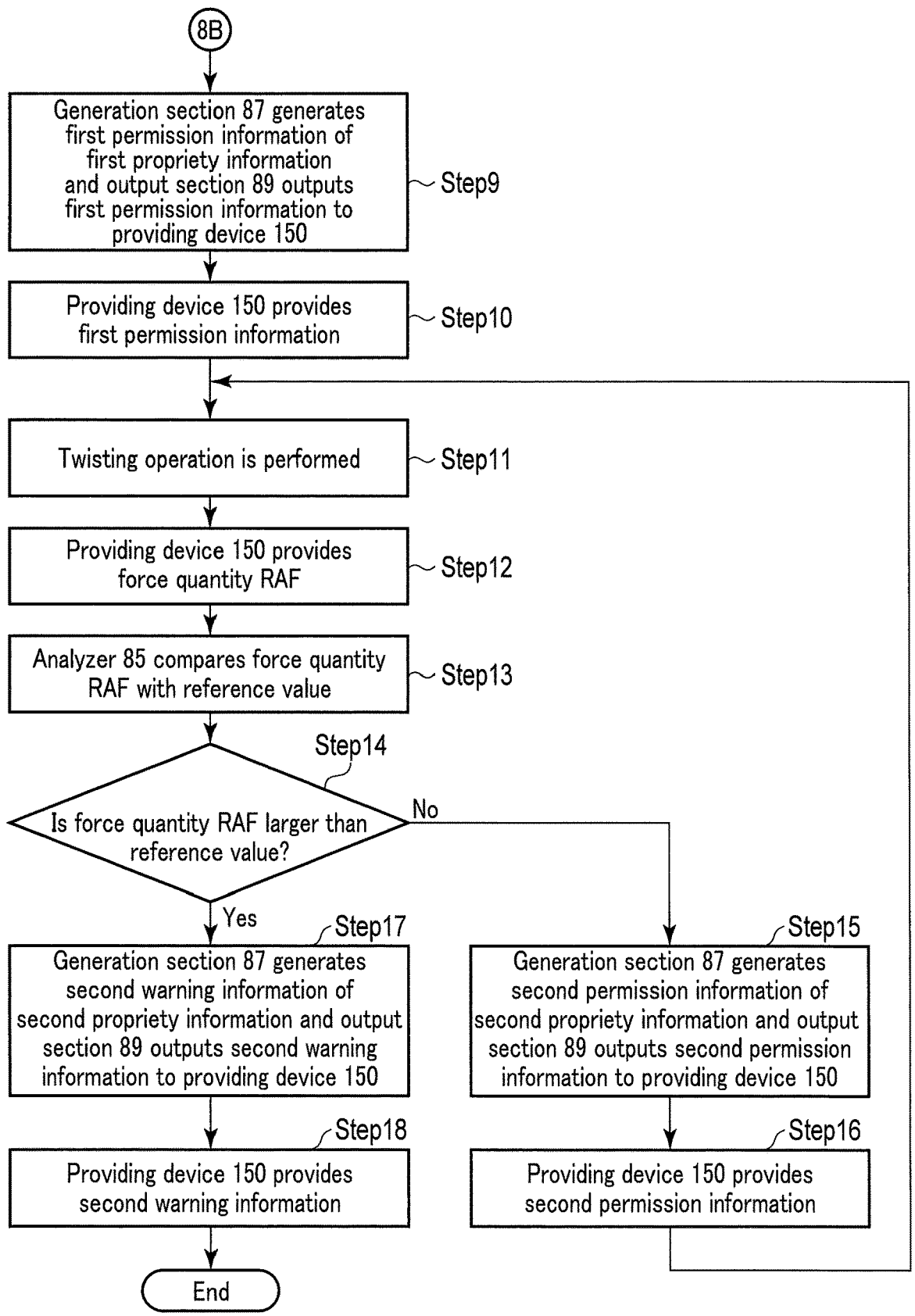
FIG. 8B is a remaining part of flowchart showing the operation method of the flexible tube insertion apparatus.

For example, if at least one of the force quantities RAF and LAF is smaller than the reference value (Step 6: No), as shown in FIG. 8B, the generation section 87 generates the first permission information of the first propriety information, and the output section 89 outputs the first permission information of the first propriety information to the providing device 150 (Step 9). The providing device 150 provides the first permission information of the first propriety information (Step 10). After the first permission information of the first propriety information is provided, the twisting operation is performed (Step 11).

In the twisting operation, the flexible tube 35 is twisted around the central axis of the flexible tube 35 in a predetermined direction (herein, the clockwise direction) so as to eliminate the loop section and change the flexible tube 35 into a substantially linear state.

The external force detector 60 calculates the force quantity RAF and outputs the calculated force quantity RAF to the output section 89. The output section 89 outputs the force quantity RAF calculated by the external force detector 60 to the providing device 150. The providing device 150 provides the force quantity RAF by, for example, displaying it in the form of the numeral value 155c (Step 12).

In addition, the external force detector 60 outputs the calculated force quantity RAF to the analyzer 85. The analyzer 85 compares the force quantity RAF with the reference value (Step 13). The analyzer 85 determines whether or not the force quantity RAF is larger than the reference value, and outputs the determination result to the generation section 87 (Step 14).

If the force quantity LAF is smaller than the reference value (Step 14: No), the generation section 87 generates the second permission information of the second propriety information, and the output section 89 outputs the second permission information of the second propriety information to the providing device 150 (Step 15). The providing device 150 provides the second permission information of the second propriety information (Step 16). After the second permission information of the second propriety information is provided, the operation returns to Step 11 in a manner such that the twisting operation is continuously performed.

If the force quantity LAF is larger than the reference value (Step 14: Yes), the generation section 87 generates the second warning information of the second propriety information, and the output section 89 outputs the second warning information of the second propriety information to the providing device 150 (Step 17). The providing device 150 provides the second warning information of the second propriety information (Step 18). After the second warning information of the second propriety information is provided, the operation is terminated.

Generally, a running state of the flexible tube 35 inside the large intestine, a length of the large intestine, and a condition of the large intestine differ widely for each patient. Such differences give variety to the tactile information for an operator when performing the twisting operation on the hand side of the flexible tube 35 using one hand while gripping the hand side of the flexible tube with the same hand, such tactile information being a sense of resistance, which is transmitted from the hand side of the flexible tube 35 to the same hand, and is sensed differently by different operators.

In the present embodiment, the tactile information is calculated by the external force detector 60, as quantitative information such as the force quantities LAF and RAF of the external forces LF and RF applied to the flexible tube 35. In the present embodiment, a relation between the force quantities LAF and RAN and the reference value is analyzed by the analyzer 85 and, based on the analysis result, the first propriety information is generated in the generation section 87 and output from the output section 89. In the present embodiment, the first propriety information is output and provided based on the force quantities LAF and RAF instead of based on the shape information of the flexible tube 35. Therefore, in the present embodiment, the tactile information can be calculated as quantitative information and, based on the calculation result, the first propriety information can be output and provided as support information for insertion.

In the present embodiment, the first warning information or the first permission information contained in the first propriety information is output. This allows an operator to clearly perceive whether or not performing the twisting operation for eliminating the loop section 39 to change the flexible tube 35 into a substantially linear state is permitted, before performing the twisting operation.

In the present embodiment, the second warning information or the second permission information contained in the second propriety information as support information for insertion is output and provided. This allows an operator to clearly perceive whether or not the twisting operation in progress is overloading a patient, during the twisting operation.

Therefore, in the present embodiment, the first propriety information and the second propriety information as support information for insertion enables the twisting operation to be performed while a kinetic load on an intestinal tract is visualized and perceived. In the present embodiment, regardless of whether an operator is a person skilled in the twisting operation (hereinafter, referred to as an expert) or a person who has low experience in the twisting operation (hereinafter, referred to as an inexperienced person), accurate support information can be equally output and provided.

In the present embodiment, it is possible to quantitatively determine whether the twisting operation is permitted based on the first propriety information before the twisting operation is performed. In the present embodiment, it is possible to quantitatively determine whether or not the twisting operation is overloading a patient based on the second propriety information, during the twisting operation. As described above, in the present embodiment, an unreasonable twisting operation can be prevented before an overload is given to an intestine tract, etc., so that the occurrence of the patient feeling pain can be prevented and the safety can be improved.

In the present embodiment, the second propriety information, which indicates whether an excessive force quantity is applied or not to the flexible tube 35 during the twisting operation currently performed to eliminate the loop section formed in the flexible tube 35 and change the flexible tube 35 into a substantially linear state, is output and provided to an operator. Accordingly, information indicative of whether or not a patient is overloaded can be output and provided to an operator. This improves the safety in an insertion operation, reduces the pain felt by a patient, and improves an arrival rate of the flexible tube 35 to a deep part.

In the present embodiment, the reference value is manually set in the example 1. In the example 2, the reference value is calculated based on a calculation condition set in advance by an operator from force quantities accumulated by the operator's discretionary determination. In the example 3, the reference value is calculated based on a calculation condition set in advance by an operator from force quantities accumulated based on an accumulation condition set in advance by the operator. Therefore, the first or second propriety information in accordance with a condition can be output and provided.

In the present embodiment, the reference value is correctable based on patient's information and model information. This allows improving the safety in an insertion operation, reducing a patient's pain, and improving an arrival rate of the flexible tube to a deep part.

In the present embodiment, in the case where only one external force detector 60 is disposed on the flexible tube, the external force detector 60 is disposed on the periphery of the gripped portion 38 of the flexible tube 35 to be gripped or the periphery of the intersecting portion 39a of the loop section 39 formed in the flexible tube 35. Thus, the force quantity at the periphery of the gripped portion 38 or the intersecting portion 39a can be reliably detected. In addition, the number of the external force detectors 60 can be minimized, and the constitution of the insertion apparatus 10 can be simplified.

In the present embodiment, for example, the external force detectors 60 are disposed to be spaced apart from each other at substantially equidistant intervals. For example, the external force detectors 60 are disposed within a range from the distal end section of the flexible tube 35 to the gripped portion 38. Therefore, in the present embodiment, it is possible to dispense with changing the arrangement position of the external force detector 60 for each patient.

In the present embodiment, the external force detector 60 may serve as both the state detector 50 as the fiber sensor and the state calculator 81. Therefore, in the present embodiment, without the need for a large and complicated device to be introduced to calculate shape information, the shape information can be calculated with a simple and compact constitution. In addition, in the present embodiment, it is possible to determine, on the monitor, the presence or absence of the loop section 39 and the position of the external force detector 60, to improve the detection accuracy of the first and second propriety information, and to perform the twisting operation on the flexible tube 35 in a state in which the shape of the flexible tube 35 is visually checked through the monitor.

The present embodiment assumes that, for example, the state detector 50 in the external force detector 60 is mounted in the form of a magnetic coil. In such a case, unless a magnetic field is in a good condition, the calculation of shape information of the flexible tube 35 or a position of the flexible tube 35 may lack accuracy, meaning the shape information or the position may not be accurately displayed on the monitor. However, the detection accuracy of the first and second propriety information can be improved by disposing the sensor 61a of the external force detector 60 in addition to the magnetic sensor of the state detector 50. In addition, unless a magnetic field is in a good condition under a situation in which the magnetic coil is used, the calculation of shape information of the flexible tube 35 or a position of the flexible tube 35 may lack accuracy, meaning that the shape information or the position may not be accurately displayed on the monitor. However, in the case of the state detector 50 being mounted in the form of the fiber sensor, there is no need to consider a magnetic field condition, and it is possible to always calculate shape information or a position with accuracy, to display the shape information or the position on the monitor with accuracy, and to provide support information.

In the present embodiment, a position of the probe 190 with respect to the flexible tube 35 in the direction of the central axis of the flexible tube 35 is adjusted by moving the probe 190. That is, the probe 190 is positioned relatively to the flexible tube 35. Therefore, a position of the external force detector 60 can be adjusted according to the patient or situation, so that the external force can be detected with high accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion support apparatus comprising:
   a processor configured to:
      generate propriety information regarding a propriety of a twisting operation of a flexible tube in accordance with a force quantity of an external force applied to the flexible tube when the flexible tube is twisted in a counterclockwise direction or a clockwise direction around a central axis of the flexible tube, the external force being detected by at least one external force detector that is disposed on the flexible tube to be inserted into the subject and configured to detect the external force;
      output the generated propriety information; and
      compare the force quantities of the external force in the counterclockwise direction and the external force in the clockwise direction with a reference value to analyze relations with the reference value, the force quantities being calculated by the at least one external force detector that is configured to detect the external force applied to the flexible tube to calculate the force quantity of the detected external force;
   wherein the propriety information is generated regarding the propriety of the twisting operation of the flexible tube in accordance with the comparison.

2. The flexible tube insertion support apparatus according to claim 1, wherein the processor generates information that is contained in the propriety information and for preventing the twisting operation from being performed, in a case where both of the force quantities of the external force in the counterclockwise direction and the external force in the clockwise direction detected by the external force detector are larger than the reference value.

3. The flexible tube insertion support apparatus according to claim 2, wherein the processor generates permission information on permission for the twisting operation, contained in the propriety information, in a case where at least one of the two force quantities of the external force in the counterclockwise direction and the external force in the clockwise direction detected by the external force detector is smaller than the reference value.

4. The flexible tube insertion support apparatus according to claim 1, wherein the processor is further configured to:
   store the force quantities calculated by the at least one external force detector;
   accumulate one or more force quantities among the stored force quantities; and
   calculate the reference value based on the accumulated force quantities.

5. The flexible tube insertion support apparatus according to claim 4, wherein the processor calculates the reference value based on a force quantity corresponding to an input calculation condition among the accumulated force quantities.

6. The flexible tube insertion support apparatus according to claim 1, wherein the force quantities correspond to any one of:
   a force quantity at a point in time when application of a given quantity of twisting to the flexible tube is completed;
   a maximum force quantity during a period from start to completion of application of the given quantity of twisting to the flexible tube;
   a value obtained by integrating a force quantity from the start to the completion of the application; and
   a value obtained by integrating the maximum force quantity during a period from the start to the completion of the application, over a period in time from before to after a point in time when the maximum force quantity is calculated.

7. The flexible tube insertion support apparatus according to claim 1, wherein:
   the propriety information includes first propriety information and second propriety information based on a comparison result between the two force quantities as measured values and the reference value;

the first propriety information indicates whether or not to permit the twisting operation in a current situation; and the second propriety information indicates whether an excessive quantity of force is applied or not to the flexible tube while the twisting operation is performed in order to eliminate a loop section formed in the flexible tube and in order to change the flexible tube into a substantially linear state.

8. The flexible tube insertion support apparatus according to claim 1, wherein in a case where external force detectors are disposed on the flexible tube, the processor is configured to:

analyze an N-th force quantity (N is a natural number of one or more) from the maximum force quantity among the force quantities in a first direction around the central axis that are respectively detected by the external force detectors, and compare the N-th force quantity and the force quantity of the external force in a direction opposite to the first direction at an arrangement position of the external force detector that has calculated the N-th force quantity, with the reference value, respectively;

analyze a portion at which a difference between a force quantity before the twisting and a force quantity after the twisting is greatest among the force quantities in the first direction around the central axis respectively detected by the external force detectors, and compare the force quantity of the external force in the counterclockwise direction and the force quantity of the external force in the clockwise direction at the portion at which the difference is greatest, with the reference value, respectively;

compare each of the force quantity of the external force in the counterclockwise direction and the force quantity of the external force in the clockwise direction that are calculated by the external force detector that is disposed at the position where a reaction force is generated by the twisting, with the reference value; or compare each of a total sum of the force quantities of the external forces in the counterclockwise direction respectively calculated by the external force detectors disposed within a desired range and a total sum of the force quantities of the external forces in the clockwise direction respectively calculated by the external force detectors disposed within the desired range, with the reference value.

9. A flexible tube insertion apparatus comprising:

a flexible tube that has flexibility and is to be inserted into a subject;

at least one external force detector that is disposed on the flexible tube and configured to detect an external force applied to the flexible tube and calculate a force quantity of the detected external force;

the flexible tube insertion support apparatus according to claim 1; and a monitor configured to display the output propriety information.

10. The flexible tube insertion apparatus according to claim 9, wherein the monitor displays the propriety information as information including at least one of characters, a symbol, and a numerical value of the force quantity.

11. The flexible tube insertion apparatus according to claim 9, wherein the at least one external force detector includes:

a sensor that is disposed on a peripheral surface of the flexible tube and configured to detect the external force; and a force quantity calculator configured to calculate the force quantity based on the external force.

12. The flexible tube insertion apparatus according to claim 9, further comprising a probe to be inserted into the flexible tube, wherein the at least one external force detector includes:

a sensor that is disposed on a peripheral surface of the probe and configured to detect the external force; and a force quantity calculator configured to calculate the force quantity based on the external force.

13. The flexible tube insertion apparatus according to claim 9, further comprising:

a state detector configured to detect state information of the flexible tube regarding a state of the flexible tube; and a state calculator configured to calculate shape information of the flexible tube regarding a shape of the flexible tube along the central axis of the flexible tube based on the state information detected by the state detector, wherein the shape information of the flexible tube includes position information of the external force detector, and the monitor displays the shape information.

14. The flexible tube insertion apparatus according to claim 13, wherein the external force detector serves as the state detector and the state calculator.

15. The flexible tube insertion apparatus according to claim 9, further comprising an input section configured to input the reference value to the processor.

16. The flexible tube insertion apparatus according to claim 9, wherein the processor is further configured to:

store the force quantities calculated by the external force detectors;

accumulate one or more force quantities among the force quantities stored in the storage section; and calculate the reference value based on the accumulated force quantities.

17. The flexible tube insertion apparatus according to claim 16, further comprising a selection setting section configured to set a calculation condition in advance to the processor and input the set calculation condition to the processor, wherein the selection setting section sets a correction value for the reference value.

18. The flexible tube insertion apparatus according to claim 9, wherein:

in a case where only one external force detector is disposed on the flexible tube, the external force detector is disposed at a position where the external force is applied to the flexible tube or a reaction force is generated by twisting; and in a case where external force detectors are disposed on the flexible tube, the external force detectors are disposed within a range from a distal end section of the flexible tube to a gripped portion of the flexible tube to be a gripped.

19. A flexible tube insertion support method of supporting insertion of a flexible tube to be inserted into a subject, the method comprising, when the flexible tube is twisted in a counterclockwise direction or a clockwise direction around a central axis of the flexible tube:

detecting an external force applied to the flexible tube;

generating propriety information regarding a propriety of a twisting operation of the flexible tube in accordance with a force quantity of the external force;

outputting the generated propriety information; and
compare the force quantities of the external force in the counterclockwise direction and the external force in the clockwise direction with a reference value to analyze relations with the reference value, the force quantities being calculated by the at least one external force detector that is configured to detect the external force applied to the flexible tube to calculate the force quantity of the detected external force;
wherein the propriety information is generated regarding the propriety of the twisting operation of the flexible tube in accordance with the comparison.

* * * * *